(12) United States Patent
Muskatello et al.

(10) Patent No.: US 7,785,296 B2
(45) Date of Patent: Aug. 31, 2010

(54) NEEDLE TIP SPRING PROTECTOR

(75) Inventors: James M. Muskatello, Southington, CT (US); Thomas F. Lilley, Jr., New Milford, CT (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

(21) Appl. No.: 12/175,068

(22) Filed: Jul. 17, 2008

(65) Prior Publication Data

US 2010/0016804 A1  Jan. 21, 2010

(51) Int. Cl.
*A61M 5/32* (2006.01)
(52) U.S. Cl. .................. 604/192; 604/198; 604/263
(58) Field of Classification Search .................. 604/192, 604/198, 110, 164.01–170.03, 272, 263–264
See application file for complete search history.

(56) References Cited

U.S. PATENT DOCUMENTS

| | | | |
|---|---|---|---|
| 1,085,505 A | 1/1914 | Stafford | |
| 3,055,364 A | 9/1962 | Myerson et al. | |
| 3,477,437 A | 11/1969 | Goldberg | |
| 4,425,120 A * | 1/1984 | Sampson et al. | 604/198 |
| 4,755,170 A | 7/1988 | Golden | |
| 4,778,453 A | 10/1988 | Lopez | |
| 4,781,692 A | 11/1988 | Jagger et al. | |
| 4,795,432 A | 1/1989 | Karczmer | |
| 4,804,371 A | 2/1989 | Vaillancourt | |
| 4,887,998 A | 12/1989 | Martin et al. | |
| 4,921,490 A | 5/1990 | Spier et al. | |
| 4,929,241 A | 5/1990 | Kulli | |
| 4,944,725 A | 7/1990 | McDonald | |
| 4,994,041 A | 2/1991 | Dombrowski et al. | |
| 5,059,180 A | 10/1991 | McLees | |
| 5,085,648 A | 2/1992 | Purdy et al. | |
| 5,092,851 A | 3/1992 | Ragner | |
| 5,129,884 A | 7/1992 | Dysarz | |
| 5,183,468 A | 2/1993 | McLees | |

(Continued)

OTHER PUBLICATIONS

International Search Report and Written Opinion received in counterpart International Patent Application PCT/US2009/04809 mailed Jan. 20, 2010 (9 pages).

*Primary Examiner*—Melba Bumgarner
*Assistant Examiner*—Edelmira Bosques
(74) *Attorney, Agent, or Firm*—Wood, Herron & Evans, LLP

(57) ABSTRACT

A needle tip spring protector for a needle having a proximal end, a distal end, and a shaft extending therebetween. The needle tip spring protector includes a spring that circumferentially surrounds a portion of the needle shaft and is restrained in a state wherein its inner diameter is large enough to allow the shaft to move freely within the spring. When the needle is moved to a position in which its distal end is at least partly within the spring, at least one of the ends of the spring releases from restraint such that the spring automatically returns to a state in which its inner diameter is sized so as to grippingly engage the shaft of the needle. Thus, after activation, the spring securely surrounds the distal end of the needle to protect healthcare workers and others from accidental contact with the needle's distal end. When used in conjunction with a catheter assembly, the needle tip spring protector may passively release from the catheter hub after the spring is automatically activated.

50 Claims, 24 Drawing Sheets

U.S. PATENT DOCUMENTS

| | | |
|---|---|---|
| 5,215,528 A | 6/1993 | Purdy et al. |
| 5,217,438 A | 6/1993 | Davis et al. |
| 5,269,765 A | 12/1993 | Kuracina |
| 5,279,591 A | 1/1994 | Simon |
| 5,295,963 A | 3/1994 | Deeks |
| 5,300,045 A | 4/1994 | Plassche, Jr. |
| 5,306,259 A | 4/1994 | Fischell et al. |
| 5,322,517 A | 6/1994 | Sircom et al. |
| 5,328,482 A | 7/1994 | Sircom et al. |
| 5,330,432 A | 7/1994 | Yoon |
| 5,334,158 A | 8/1994 | McLees |
| 5,336,199 A | 8/1994 | Castillo et al. |
| 5,344,408 A | 9/1994 | Partika |
| 5,364,370 A | 11/1994 | Szerlip |
| 5,376,080 A | 12/1994 | Petrussa |
| 5,419,766 A | 5/1995 | Chang et al. |
| 5,458,658 A | 10/1995 | Sircom |
| 5,466,223 A | 11/1995 | Bressler et al. |
| 5,472,430 A * | 12/1995 | Vaillancourt et al. ........ 604/198 |
| 5,478,313 A | 12/1995 | White |
| 5,558,651 A | 9/1996 | Crawford et al. |
| 5,569,202 A | 10/1996 | Kovalic et al. |
| 5,584,809 A | 12/1996 | Gaba |
| 5,611,781 A * | 3/1997 | Sircom et al. .......... 604/164.08 |
| 5,613,500 A | 3/1997 | Bishop |
| 5,662,610 A | 9/1997 | Sircom |
| 5,665,072 A | 9/1997 | Yoon |
| 5,718,688 A | 2/1998 | Wozencroft |
| 5,743,891 A | 4/1998 | Tolkoff et al. |
| 5,795,336 A | 8/1998 | Romano et al. |
| 5,800,395 A | 9/1998 | Botich et al. |
| 5,800,404 A | 9/1998 | Poulsen |
| 5,853,393 A | 12/1998 | Bogert |
| 5,865,806 A | 2/1999 | Howell |
| 5,879,337 A | 3/1999 | Kuracina et al. |
| 5,882,337 A | 3/1999 | Bogert et al. |
| 5,882,342 A | 3/1999 | Cooper et al. |
| 5,893,845 A | 4/1999 | Newby et al. |
| 5,911,705 A | 6/1999 | Howell |
| 5,914,168 A | 6/1999 | Wakamatsu et al. |
| 5,919,168 A * | 7/1999 | Wheeler ..................... 604/198 |
| 6,001,080 A | 12/1999 | Kuracina et al. |
| 6,096,005 A * | 8/2000 | Botich et al. ................ 604/110 |
| 6,210,374 B1 | 4/2001 | Malencheck |
| 6,221,047 B1 | 4/2001 | Greene et al. |
| 6,228,054 B1 | 5/2001 | Dysarz |
| 6,443,927 B1 | 9/2002 | Cook |
| 6,443,929 B1 | 9/2002 | Kuracina et al. |
| 6,511,461 B2 | 1/2003 | Jönsson |
| 6,524,278 B1 | 2/2003 | Campbell et al. |
| 6,544,231 B1 | 4/2003 | Palmer et al. |
| 6,547,764 B2 | 4/2003 | Larsen et al. |
| 6,558,354 B1 | 5/2003 | Howell |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,623,458 B2 | 9/2003 | Woehr et al. |
| 6,629,959 B2 | 10/2003 | Kuracina et al. |
| 6,632,198 B2 | 10/2003 | Caizza |
| 6,673,044 B2 | 1/2004 | Righi et al. |
| 6,689,102 B2 | 2/2004 | Greene |
| 6,695,814 B2 | 2/2004 | Greene et al. |
| 6,706,019 B1 | 3/2004 | Parker et al. |
| 6,712,787 B1 | 3/2004 | Dysarz |
| 6,716,197 B2 | 4/2004 | Svendsen |
| 6,726,658 B2 | 4/2004 | Hochman |
| 6,776,777 B2 | 8/2004 | Barrelle |
| 6,786,875 B2 | 9/2004 | Barker et al. |
| 6,796,962 B2 | 9/2004 | Ferguson et al. |
| 6,811,545 B2 | 11/2004 | Vaillancourt |
| 6,860,871 B2 | 3/2005 | Kuracina et al. |
| 6,869,415 B2 | 3/2005 | Asbaghi |
| 6,872,193 B2 | 3/2005 | Shaw et al. |
| 6,905,478 B2 | 6/2005 | Ingram et al. |
| RE38,996 E | 2/2006 | Crawford et al. |
| 6,994,690 B2 | 2/2006 | Kiehne |
| 7,004,927 B2 | 2/2006 | Ferguson et al. |
| 7,008,402 B2 | 3/2006 | Ferguson et al. |
| 7,014,622 B1 | 3/2006 | Pressly, Sr. et al. |
| 7,014,623 B2 | 3/2006 | Prestidge et al. |
| 7,018,344 B2 | 3/2006 | Bressler et al. |
| 7,041,086 B2 | 5/2006 | Yang |
| 7,041,092 B2 | 5/2006 | Barrelle |
| 7,083,600 B2 | 8/2006 | Meloul |
| 7,172,576 B2 | 2/2007 | Sawa et al. |
| 7,201,740 B2 | 4/2007 | Crawford |
| 7,220,247 B2 | 5/2007 | Shaw et al. |
| 7,255,689 B2 | 8/2007 | Westbye |
| 7,300,416 B2 | 11/2007 | Botich et al. |
| 7,344,517 B2 | 3/2008 | Schiller |
| 7,354,422 B2 | 4/2008 | Riesenberger et al. |
| 7,393,344 B2 | 7/2008 | Mohammed |
| 2003/0144627 A1 | 7/2003 | Woehr et al. |
| 2004/0019332 A1 | 1/2004 | Grabis et al. |
| 2004/0030294 A1 | 2/2004 | Mahurkar |
| 2004/0049155 A1 | 3/2004 | Schramm |
| 2004/0097887 A1 | 5/2004 | Secrest et al. |
| 2004/0116854 A1 | 6/2004 | Abulhaj et al. |
| 2004/0225260 A1 | 11/2004 | Villa et al. |
| 2005/0107740 A1 | 5/2005 | Jensen et al. |
| 2005/0113750 A1 | 5/2005 | Targell |
| 2005/0159705 A1 | 7/2005 | Crawford et al. |
| 2005/0182363 A1* | 8/2005 | Kulli .......................... 604/110 |
| 2006/0089597 A1 | 4/2006 | Allard |
| 2006/0100588 A1 | 5/2006 | Brunnberg et al. |
| 2006/0116638 A1 | 6/2006 | Woehr et al. |
| 2007/0129674 A1* | 6/2007 | Liversidge .................. 604/110 |

* cited by examiner

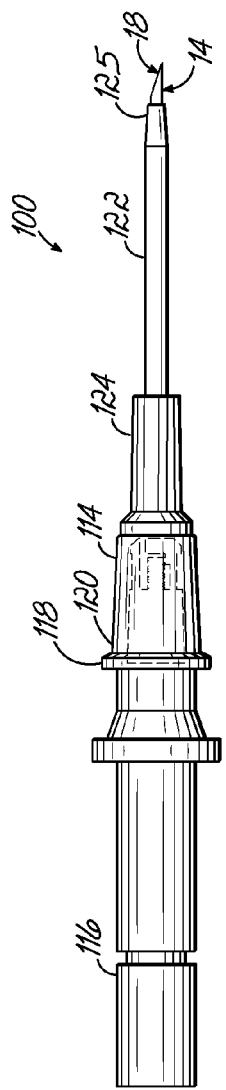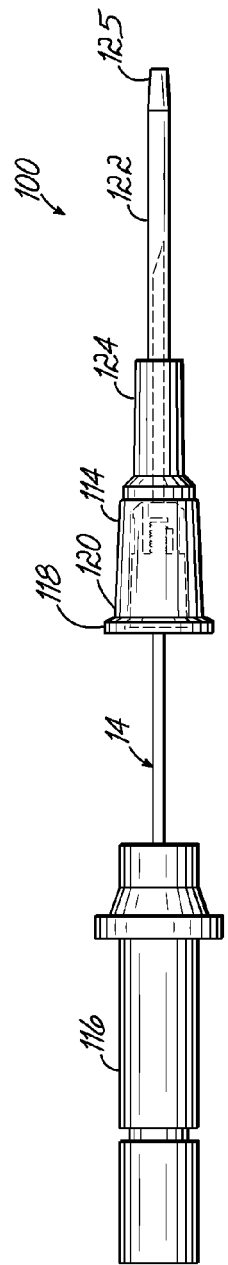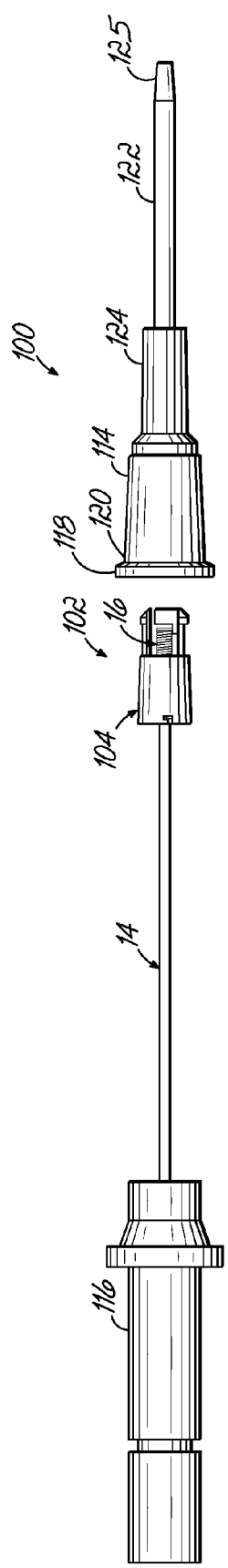

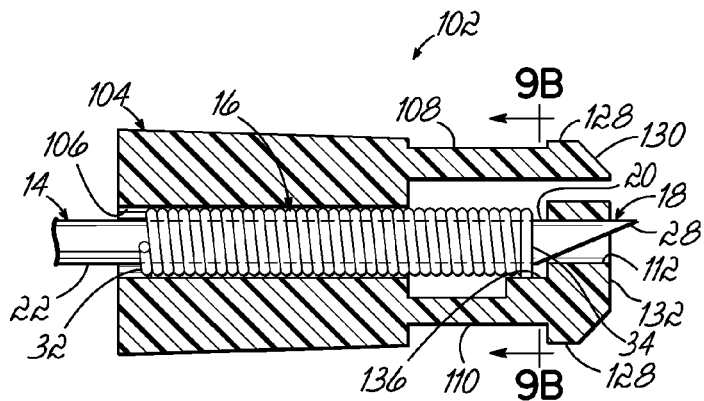
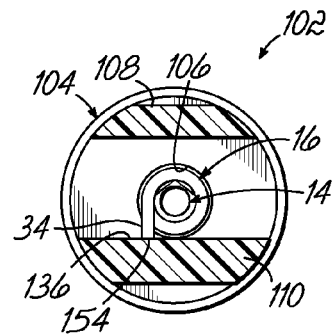
FIG. 9A  FIG. 9B
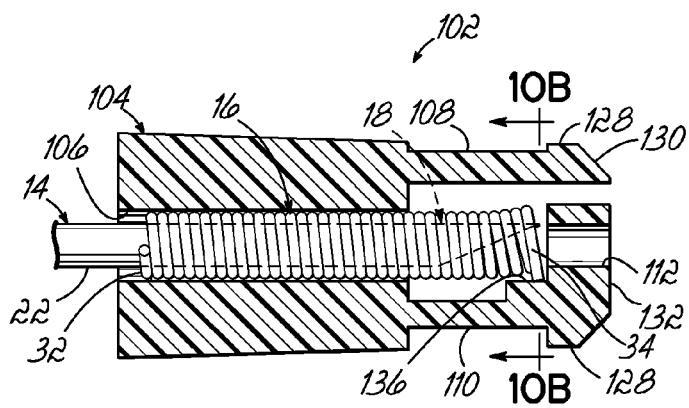
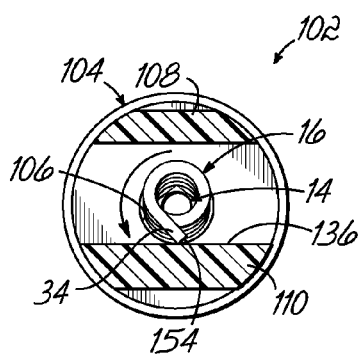
FIG. 10A  FIG. 10B
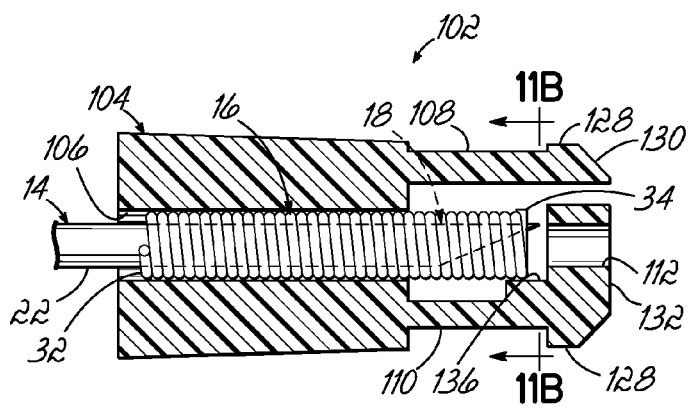
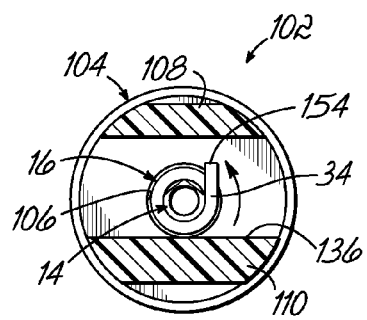
FIG. 11A  FIG. 11B

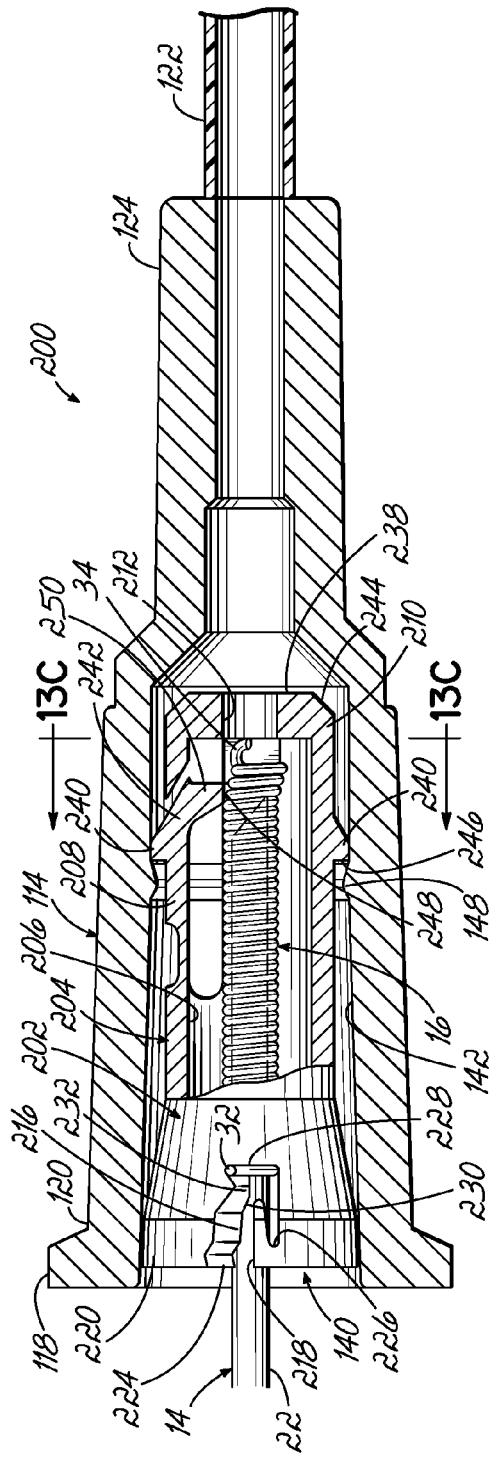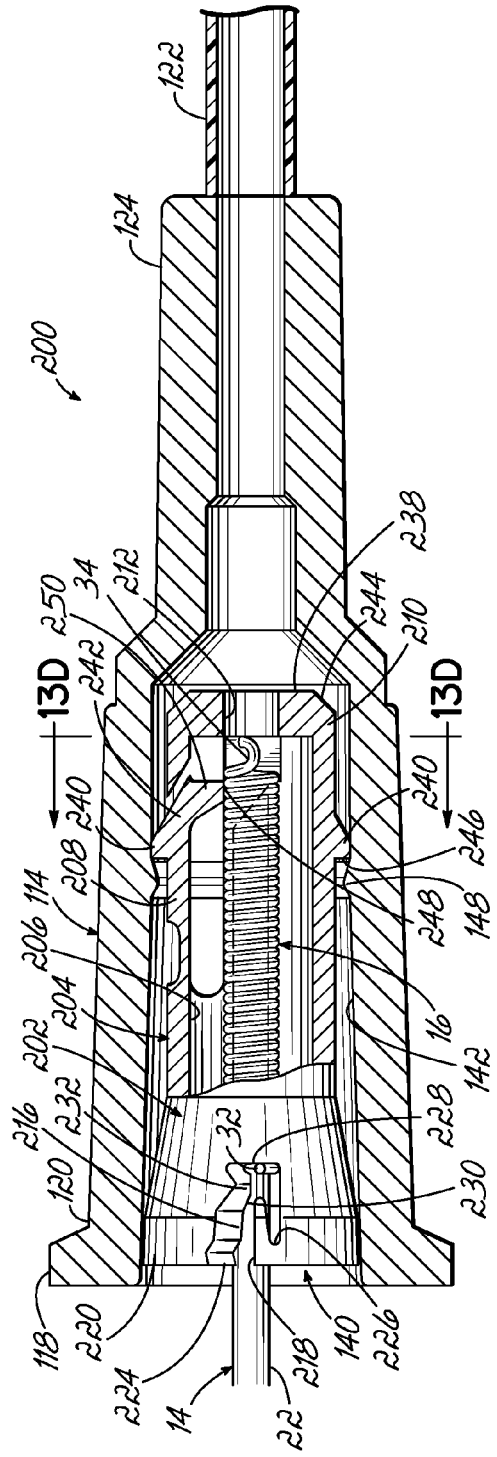

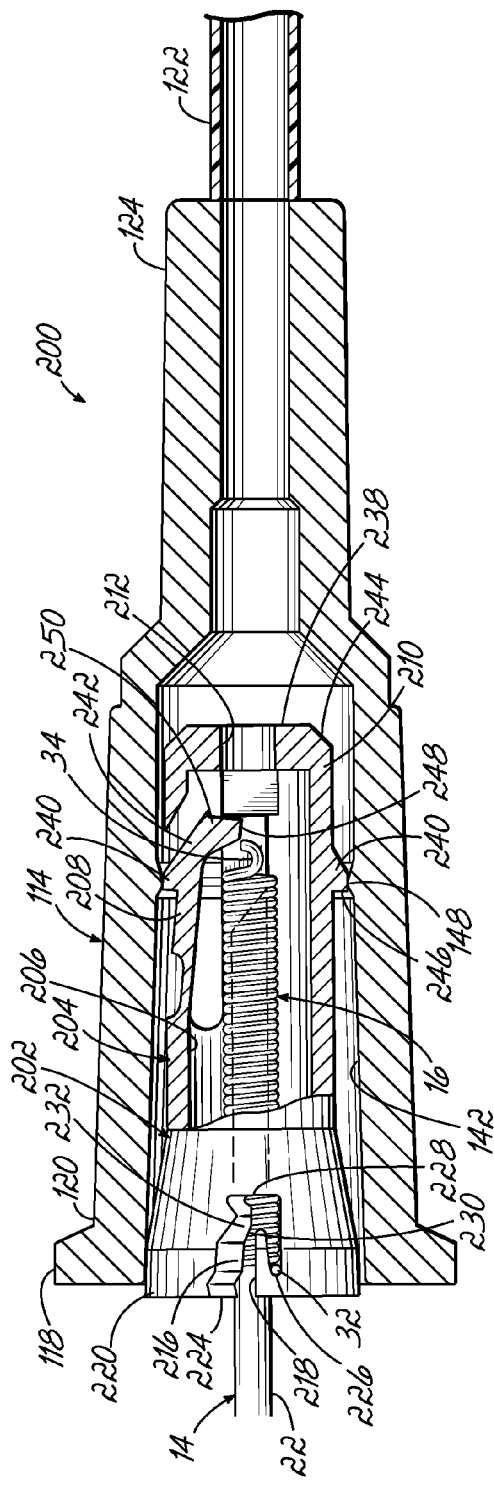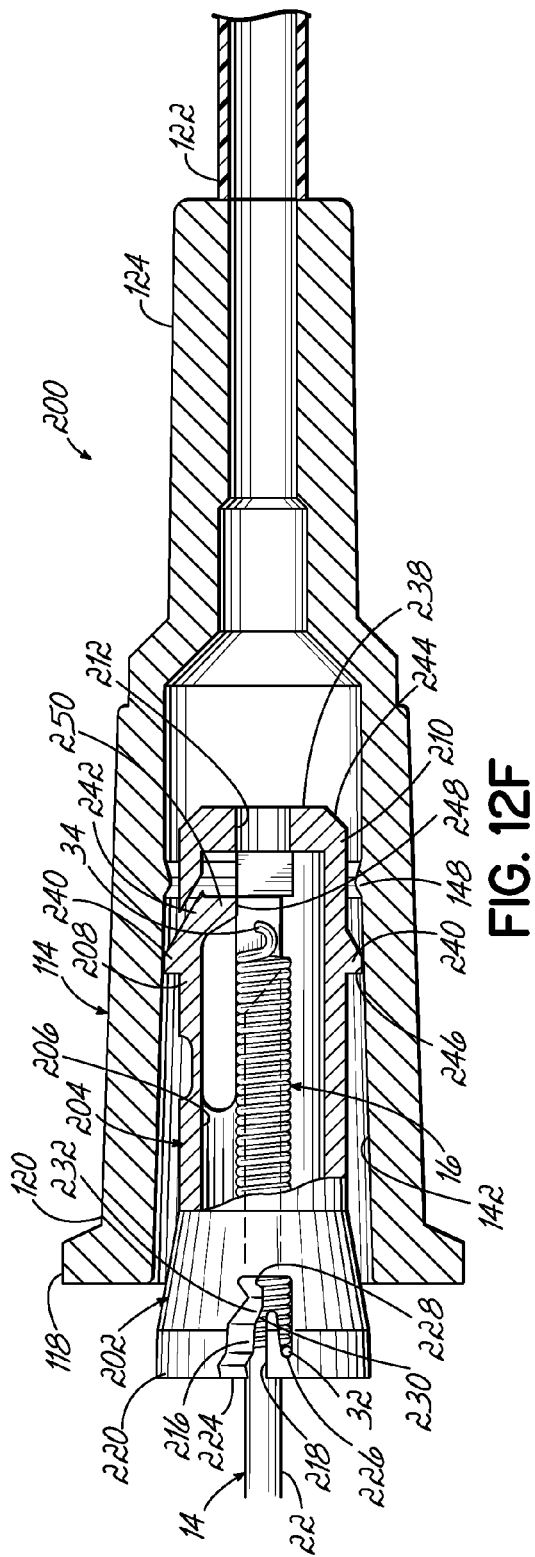

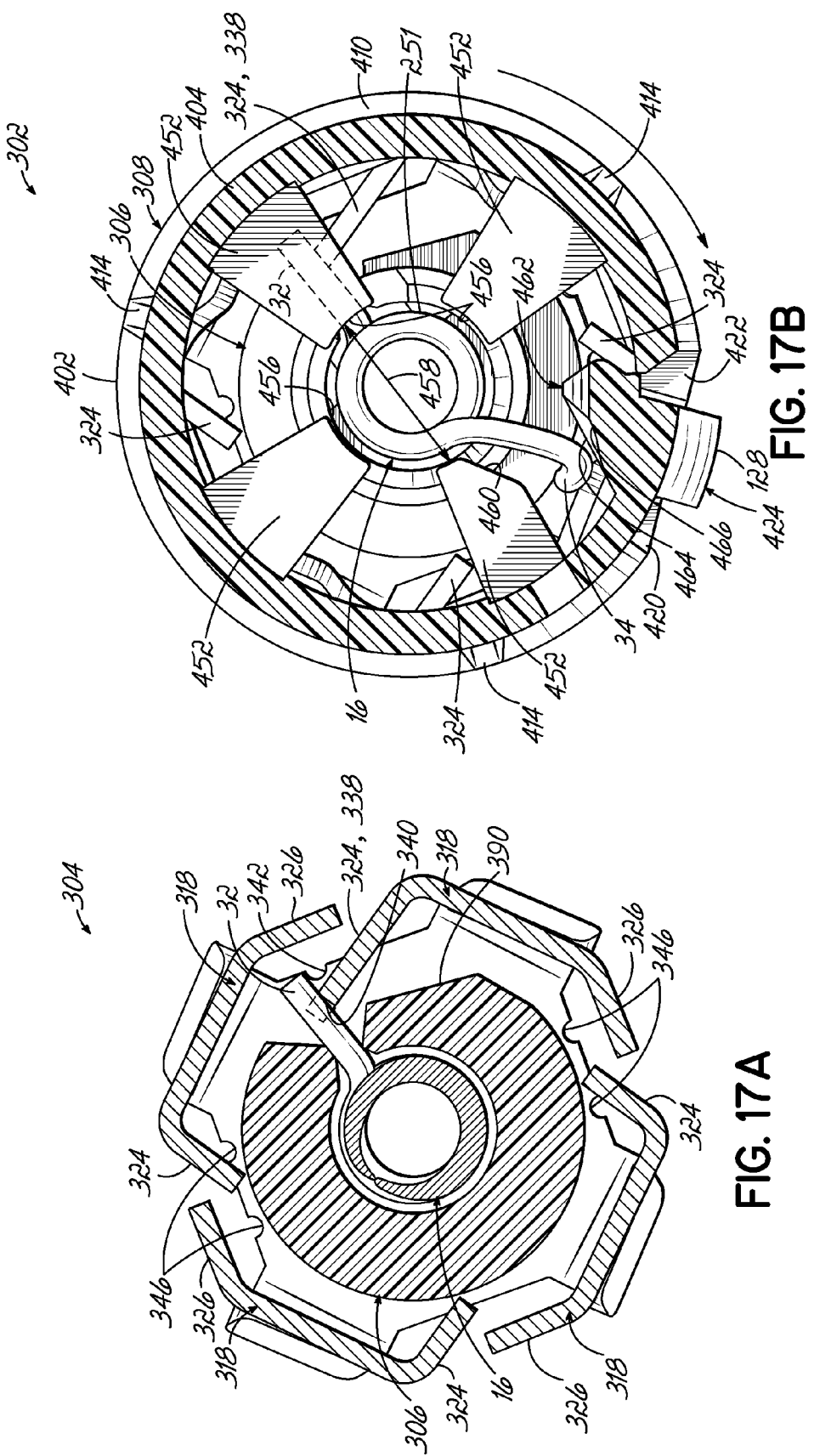

ial length of the needle. Still others require alteration of the shape or surface of the needle or tethering or other attachment to the cannula hub to prevent the needle tip protector from coming off the needle.

NEEDLE TIP SPRING PROTECTOR

TECHNICAL FIELD

The present invention relates to medical needles (such as hypodermic needles, catheter insertion needles or cannulae, or other sharp-tipped hollow or solid cannulae) and, more particularly, to devices that shield the sharp tip of the needle after withdrawal from a patient.

BACKGROUND

A variety of different needle tip protectors have been developed or proposed to protect, i.e., to enclose or otherwise shield, sharp needle tips in recognition of the need to reduce or eliminate accidental needle-sticks. Some needle tip protectors include mechanisms having many different cooperating parts. Such needle tip protectors are often unreliable and difficult to manufacture. Other needle tip protectors require the healthcare worker to activate the protection device through a trigger mechanism or other activator. Thus, instead of being passively activated, such devices require additional steps before they offer protection. Still other needle tip protectors require longer needles than normally would be used in a nonprotected version for their respective gauge, especially where the needle protector is large and consumes some of the available axial length of the needle. Still others require alteration of the shape or surface of the needle or tethering or other attachment to the cannula hub to prevent the needle tip protector from coming off the needle.

One example of a needle tip protector is described in U.S. Pat. Nos. 5,328,482 and 5,322,517. These patents disclose the broad concept of a coil spring disposed about a needle shaft in a wound state, and which can unwind to grip the needle shaft. More specifically, the needle is disposed through a passageway formed by the interior of the coil spring. One end of the spring is fixed relative to the other end, and may be rotated ("wound") against the rotational bias of the spring to expand the diameter of the passageway. Upon release, the spring unwinds to reduce the diameter of the passageway to grip the needle shaft.

However, the needle tip protector of U.S. Pat. Nos. 5,328, 482 and 5,322,517 involves many components and cooperating parts and thus involves complex and costly manufacture. For example, the spring is held in its wound configuration by a separate rotational latch and will unwind only upon release of this separate latch. Further, the housing of the device includes concentric outer and inner cores. The outer core is moved relative to the inner core to wind the spring. Once the latch has been released to allow the spring to unwind and grip a needle, these cores must be prevented from moving relative to one another to prevent inadvertent rewinding of the spring. Thus, a second spring that prevents rotation of the outer core is provided. As a result, this needle tip protector suffers the drawbacks of complexity described above.

SUMMARY

The present invention provides a needle tip spring protector that overcomes the various disadvantages and drawbacks of prior approaches. To this end, and in accordance with the principles of the present invention, a spring surrounds a needle and contacts a bearing surface such that the needle can move within the spring, but the spring can move away from the bearing surface to grip the needle once the needle is retracted. More specifically, the spring normally has an inner diameter sized to grippingly engage the shaft of the needle, and can be wound to an armed state having an inner diameter sized to allow the needle to pass therethrough. The spring is held in the armed state, contacting the bearing surface, until the needle tip is pulled towards, and possibly into, the spring, at which time the spring moves out of contact with the bearing surface to unwind to a gripping state, thus preventing further axial movement of the needle relative to the spring. In this manner, the spring is self-activating and does not require separate mechanisms to release the spring as with certain prior needle tip spring protectors.

To achieve the armed state, the spring includes first and second aspects that can be wound relative to one another. For example, the first aspect of the spring can be restrained by a housing such that the second aspect of the spring may be wound relative thereto, thereby changing the inner diameter of the spring. In other words, when the spring is "wound," the first aspect of the spring can be restrained while the second aspect of the spring is rotated against the rotational bias of the spring. As a result, the spring can be configured in a gripping state with an inner diameter sized to grippingly engage the needle shaft, or in an armed state in which the inner diameter is expanded so as to permit axial movement of the needle relative to the spring.

The apparatus of the present invention may be used with hypodermic needles or other needles, such as in a catheter insertion apparatus. When used with a catheter insertion apparatus, the bearing surface may be on the interior of a catheter hub, the bearing surface may be part of a housing (including a passage for the needle) separate from a catheter hub, or the bearing surface may be another portion of the spring itself. When a separate housing is used, the needle tip need not be retracted completely into the spring provided it has been retracted into the housing before the spring releases, although the tip may be surrounded by the spring such that it is protected by both the spring and the housing. Either way, the needle tip is protected so as to reduce or eliminate the potential for accidental needle-sticks.

In accordance with yet a further aspect, when the spring grips the needle, a gripping force between the spring and needle is greater than a holding force between the housing and the catheter hub. Consequently, continued retraction of the needle will remove the needle completely from the catheter hub, along with the needle tip spring protector. The apparatus of the present invention may be configured such that the housing will only release from the catheter hub after the spring has moved from the armed state to the gripping state to grippingly engage the needle. Moreover, the spring and housing may be configured so as to allow the entire spring to rotate relative to the housing when in the gripping state. This would prevent, for example, a rewinding of the spring after actuation. The spring and any housing may be sized to cooperate with the catheter hub such that a standard length needle cannula for the respective gauge of the catheter may be used, although longer needles may be used if desired. Further, while surface changes and tethers may be used, the gripping engagement of the spring to the needle limits further axial movement of the needle such that there is no requirement to alter the surface of the needle or to use tethers or the like.

Thus, the needle tip spring protector of this invention requires relatively few parts. Further, this invention provides a needle tip spring protector which overcomes the various disadvantages and drawbacks of prior approaches, but does so in a simple and low-cost manner and enables use of standard size and shaped needles and without the need for tethering and the like. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention, and together with the general description of the invention given above, and the detailed description of the embodiments given below, serve to explain the principles of the present invention.

FIGS. 3A-3C are side views of a catheter assembly including a second embodiment of a needle tip spring protector in accordance with the principles of the present invention;

FIGS. 9A and 9B are cross-sectional side and cross-sectional end views of the needle tip spring protector of FIG. 4 when the needle extends through the spring in an armed state;

FIGS. 10A and 10B are cross-sectional side and cross-sectional end views that depict the changes that occur in the needle tip spring protector of FIGS. 9A and 9B as the spring transitions from the armed state to the activated state;

FIGS. 11A and 11B are cross-sectional side and cross-sectional end views that depict the needle tip spring protector of FIGS. 10A and 10B after the spring reaches the activated state;

FIG. 12C is a cross-sectional elevational view of the catheter assembly of FIG. 12B after retracting the needle.

FIG. 12D a cross-sectional elevational view of the catheter assembly of FIG. 12C with the spring in the gripping state.

FIG. 12E a cross-sectional elevational view of the catheter assembly of FIG. 12D with the spring retracted to its first axial position, and the resilient arms flexing.

FIG. 12F a cross-sectional elevational view of the catheter assembly of FIG. 12E with the needle and needle tip spring protector nearly removed.

FIG. 17A is a cross-sectional view as indicated in FIG. 17;

FIG. 17B is a cross-sectional view as indicated in FIG. 17;

DETAILED DESCRIPTION

Figure 1A:
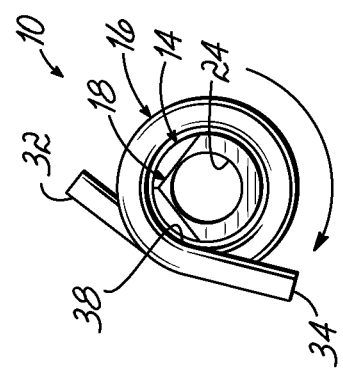
FIG. 1A is an end view of the needle and spring of FIG. 1.
Figure 2A:
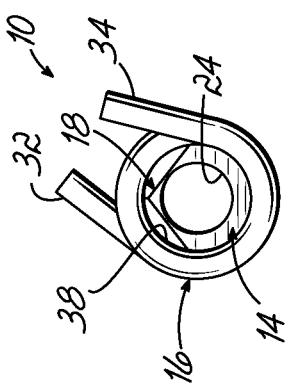
FIG. 2A is an end view of the needle and spring of FIG. 2.
Figure 1:
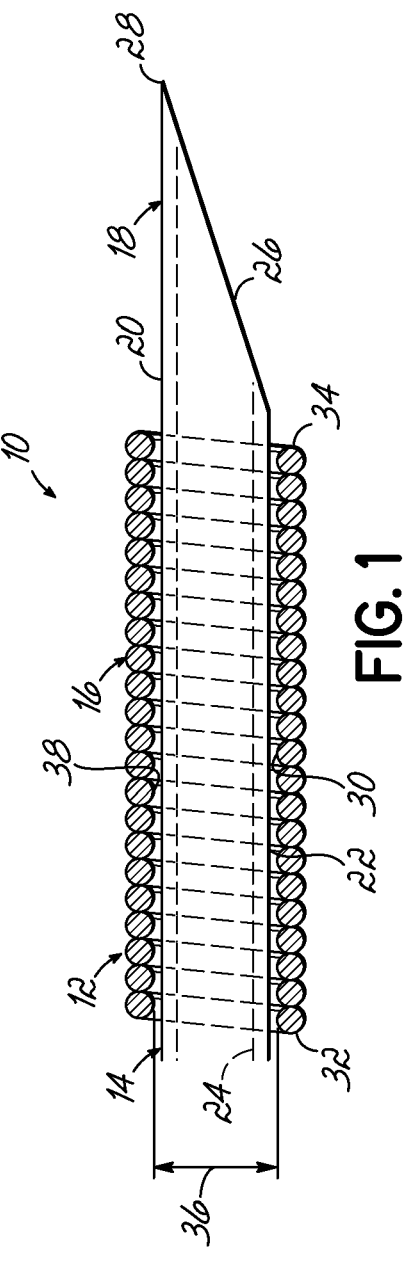
FIG. 1 is a cross-sectional view of a first embodiment of a needle tip spring protector, depicting a portion of a needle in an extended position relative to a torsion spring in an armed state such that the needle can move relative to the spring.
Figure 2:
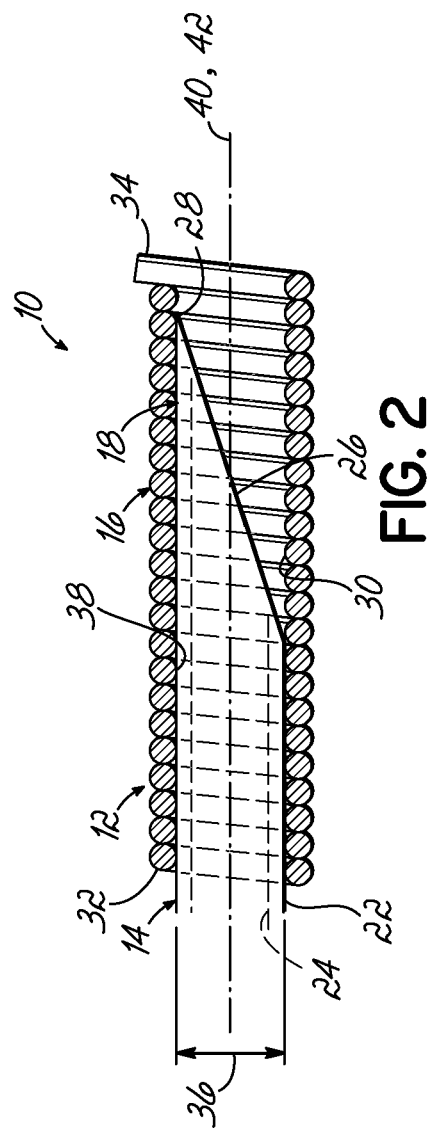
FIG. 2 is a cross-sectional view of the portion of the needle of FIG. 1 now in a retracted position relative to the torsion spring in an activated state such that the spring grippingly engages the shaft of the needle.

With reference to FIGS. 1-2A, there is shown one embodiment of a needle tip spring protector 10 that includes a resilient member 12 to surround a needle 14 in accordance with this invention. In the illustrated embodiment, the resilient member 12 is shown as a spring 16. Thus, one embodiment of the needle tip spring protector 10 may include simply a spring 16 surrounding a needle 14 (such as when used with a hypodermic needle). However, the needle 14 may be any of a variety of medical needles. Accordingly, one of ordinary skill will recognize that the needle tip spring protector described herein will operate with conventional needles as well as with cannulae for catheter assemblies and the like.

In FIG. 1, a tip 18 of the needle 14 is exposed so that the needle 14 may be used for penetration into a body of a patient. In the description provided herein, the labeling convention will be that the tip 18 is at the distal end 20 of the needle 14. Thus, when various other components are described herein, their respective distal ends will be the end that is furthest from a healthcare worker (and nearest the patient) and the proximal end will be the end closest to the healthcare worker (and furthest from the patient).

The needle 14 includes a shaft 22 with a hollow chamber 24 that operates as a fluid passageway through needle 14. The shaft 22 extends from the distal end 20 in a proximal direction to a proximal end (not shown). The tip 18 of the needle 14 includes a region 26 that varies in diameter from a nominal diameter of shaft 22 to a sharp point 28. In FIGS. 1 and 1A, a portion of the needle shaft 22 is circumferentially surrounded by the spring 16. The spring 16 defines a passage 30 through which the needle 14 passes and includes a proximal end 32 and a distal end 34. The proximal and distal ends 32, 34 are movable relative to one another such that if, for example, the proximal end 32 were restrained, the distal end 34 could be wound by rotating it against the rotational bias of the spring 16.

The spring 16 may be a conventional torsion spring, which has a rest state defined as when the spring is not restrained by any objects, and includes a particular inner diameter 36. Stainless steel, piano wire, and other similar materials are examples of materials which may be used to construct spring 16. Such a spring 16 is typically constructed from uniformly round stock formed into a plurality of turns. However, spring stock having other cross-section profiles, such as rectangular, may be used as well. Thus, while a cross-section of the spring 16 may be circular, it will be recognized by those skilled in the art that it need not be of any particular shape, so long as the inner surface 38 includes a plurality of contact points that create a virtual or effective inner diameter. These contact points are the locations where the inner surface 38 of the spring 16 contacts the needle shaft 22 to grip the shaft 22 when the spring 16 is in a gripping state. The diameter 36 is larger when spring 16 is in the gripping state than when spring 16 is in the rest state. Further, one of ordinary skill will recognize that the physical size of the spring 16 may depend on the needle 14. Thus, for a particular application, the spring 16 is selected to permit movement of the needle 14 when the spring 16 is in its wound or armed state but will grippingly engage the needle 14 once the spring 16 moves to its gripping state while trying to unwind toward its rest state.

The spring 16 includes a first aspect and a second aspect, which may be ends of the spring 16 that are capable of being wound relative to one another such that the inner diameter 36 of the spring 16 increases. More specifically, when the first aspect, such as the distal end 34, of the spring 16 is "wound," a rotational force is applied to the first aspect against the rotational bias of the spring 16, while the second aspect, such as the proximal end 32, remains fixed. This winding expands the inner diameter 36 of the spring 16 by moving the inner surface 38 of the spring 16 radially outward. When wound, the spring 16 is in an armed state and includes stored energy capable of moving the spring 16 toward its rest position. To maintain the armed state, the distal end 34 is restrained from moving, at least temporarily. It will be recognized that the first aspect may be wound while the second aspect is held in a fixed position; the second aspect may be wound while the first aspect is held in a fixed position; or the first and second aspects may each be wound in directions opposite to one another. Further, it is not necessary for the inner diameter 36 to be expanded such that the inner surface 38 of the spring 16 does not contact the needle 14, so long as the needle 14 is not gripped, and can move axially relative to the spring 16.

FIGS. 1 and 1A illustrate the needle 14 in a first, extended position and the spring 16 in the armed state such that its inner diameter 36 permits the needle 14 to slide through the passage 30 of spring 16. In this configuration, the spring 16 is able to remain relatively motionless with respect to a patient while the needle 14 is withdrawn from the patient.

FIGS. 2 and 2A illustrate the needle 14 in a second, retracted position and the spring 16 in a gripping state. In this regard, the needle 14 is moved to the retracted position by moving it in a proximal direction such that the tip 18 thereof is moved towards the spring 16. When the needle 14 is retracted to a position such that at least a portion of the tip 18 is proximal of the distal end 34 of the spring 16, the restraint on the distal end 34 of the spring 16 is removed such that the distal end 34 is allowed to rotate in the direction of the rotational bias of the spring 16. As this occurs, the spring 16 moves toward its rest state (and its gripping state) such that the inner diameter 36 of the spring 16 decreases and approaches the outer diameter of needle 14 and grips thereto in the gripping state of the spring 16.

More specifically, when the needle 14 is in the extended position (FIGS. 1 and 1A), at least a portion of the needle 14 is disposed within the spring 16. The spring 16 having a spring axis 40, is held in substantial coaxial alignment with the needle 14 having a needle axis 42, due to the presence of the needle 14 within the passage 30 of the spring 16. As the needle 14 is retracted (FIGS. 2 and 2A), the distal end 34 of the spring 16 will move to a point that allows at least a portion of the spring 16, such as the distal end 34, to move relative to the needle 14. This allows the spring 16 to move away from (see FIG. 10A, for example) a bearing surface (not shown) to then rotate in the direction of the rotational bias of the spring 16. The spring 16 may move out of contact with a bearing surface (not shown) due to a portion of the spring 16 moving out of substantial coaxial alignment with the needle 14, or due to an alteration of space between a portion of the needle 14, such as region 26, and the spring 16. The spring 16 may then rotate or unwind. As a result, the inner diameter 36 of the spring 16 is reduced to the gripping state so that spring 16 grippingly engages shaft 22. In the configuration of FIGS. 2 and 2A, therefore, the needle 14 and the spring 16 are engaged such that the needle 14 cannot move relative to the spring 16. Because the spring 16 securely engages the outside of the shaft 22, the needle tip 18 remains protected even though the needle 14 may continue to be moved relative to a patient or when it is subjected to forces that could reasonably occur during subsequent handling of the needle 14.

Accordingly, the spring 16 may substantially surround the tip 18 and protect healthcare workers from accidental contact with the tip 18. Although FIG. 2 shows the entire tip 18 enclosed within the spring 16, other embodiments described later contemplate only a portion of the tip 18 enclosed within the spring 16 (with the remainder otherwise protected, such as within a housing). Thus, as used herein, when the tip 18 of the needle 14 is described as being enclosed within the spring 16, such description may include the tip 18 entirely within the spring 16 or only a portion of the tip 18 within the spring 16. In either case, the spring 16 provides a simple-to-manufacture, reliable, easily actuated, and inexpensive means to protect a healthcare worker from inadvertent contact with the needle tip 18.

With reference to FIGS. 3A-3C, there is shown a catheter assembly 100 including a second embodiment of a needle tip spring protector 102. The needle tip spring protector 102 may include essentially the same spring 16 as the needle tip spring protector 10 of FIGS. 1-2A, but needle tip spring protector 102 also includes a housing 104 having a passage 106 (FIG. 4) for receiving needle 14 therethrough, and first and second resilient arms 108, 110. At least one of the resilient arms 108, 110 defines a passage 112 (FIG. 4) generally axially aligned with passage 106 for receiving needle 14 therethrough. First and second resilient arms 108, 110 interact with a catheter hub 114 to control release of needle tip spring protector 102 from catheter hub 114.

FIG. 3A depicts the catheter assembly 100 as an assembled unit that is in a position to be inserted within a patient. The catheter assembly 100 includes a needle hub 116 with needle 14 extending distally therefrom. Catheter hub 114 of catheter assembly 100 includes a luer fitting 118 on a proximal end 120 and a catheter tube 122 extending distally from a distal end 124. Needle shaft 22 extends through housing 104, spring 16, catheter hub 114, and catheter tube 122, with an exposed tip 18 exiting a distal end 125 of the catheter tube 122 in a first, extended position of needle 14.

The needle tip spring protector 102 is configured to permit motion of the needle 14 relative to the needle tip spring protector 102. In a manner similar to that discussed with respect to FIG. 1, the shaft 22 of the needle 14 is permitted to move freely through the needle tip spring protector 102 in a generally proximal direction such that the needle 14 moves while the needle tip spring protector 102 remains relatively motionless relative to a patient. Thus, needle hub 116 is pulled proximally relative to needle tip spring protector 102 to begin to withdraw needle 14 and to begin to separate needle hub 116 from housing 104 of needle tip spring protector 102, as seen in FIG. 3B. Once the needle 14 is moved to a position in which the needle tip 18 is located within the needle tip spring protector 102, then the spring 16 of the needle tip spring protector 102 will move to grippingly engage the needle 14 similar to the manner described with respect to FIG. 2. Once the spring 16 grippingly engages the needle 14, then the needle 14 has limited movement relative to the needle tip spring protector 102. Accordingly, continued retraction of the needle 14 will result in the configuration of FIG. 3C in which the needle tip spring protector 102 is attached around the tip 18 of the needle 14 and disengages from the inside of the catheter hub 114. Thus, healthcare workers are protected from inadvertent contact with the tip 18 of the needle 14 and the catheter tube 122 remains inserted within the patient.

Figure 4:
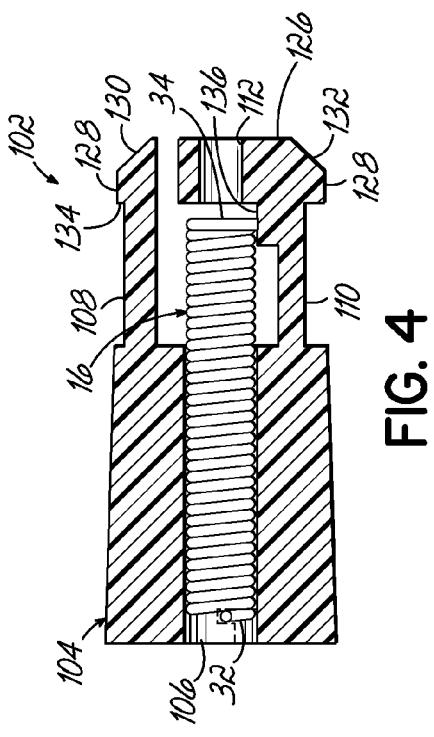
FIG. 4 is a cross-sectional view of the second embodiment of the needle tip spring protector of FIGS. 3A-3C of the present invention.

With further reference to FIG. 4, the needle tip spring protector 102 includes housing 104 having passage 106 through which the needle 14 can pass. The material of the housing 104 may be plastic, stainless steel, non-reactive metal and other similar materials. A distal end 126 of the housing 104 includes first resilient arm 108 and second resilient arm 110. The second resilient arm 110 includes passage 112 generally axially aligned with passage 106. At least one arm, and as in the illustrated embodiment, both of arms 108, 110, may include a detent 128 at distal ends 130, 132 of first and second resilient arms 108, 110, respectively, to define segments of an annular ring 134. The first and second resilient arms 108, 110 interact with features of the catheter hub 114, as explained below, to control the release of the needle tip spring protector 102 from the catheter hub 114. The first and second resilient arms 108, 110 are exemplary in nature, however, and the present invention contemplates embodiments in which the housing 104 includes one resilient arm, or includes more than two resilient arms.

Spring 16 is disposed at least partially in passage 106 and extends therefrom in the illustrated embodiment. The second resilient arm 110 includes a bearing surface 136 on which the distal end 34 of the spring 16 engages. In the particular embodiment of FIG. 4, the bearing surface 136 is generally flat and parallel with the distal end 34 of the spring 16.

Figure 5:
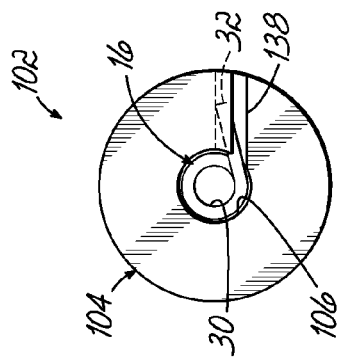
FIG. 5 is an end view of the second embodiment of the needle tip spring protector of FIG. 4.

With reference to FIG. 5, a channel 138 or similar means is shown that constrains the proximal end 32 of the spring 16. The proximal end 32 will bear against a rigid side of the channel 138, preventing the proximal end 32 from moving (e.g., rotating) relative to the housing 104. Thus, returning to FIG. 4, when the distal end 34 of the spring 16 is wound against the rotational spring bias relative to the proximal end 32 of the spring 16, and restrained against the bearing surface 136, the spring 16 will be in an armed state having passage 30 including inner diameter 36 through which needle 14 can pass. The passage 30 is sized large enough to accept the needle 14 but sized small enough that needle 14, when present, prevents the second resilient arm 110 from flexing or moving.

Figure 6:
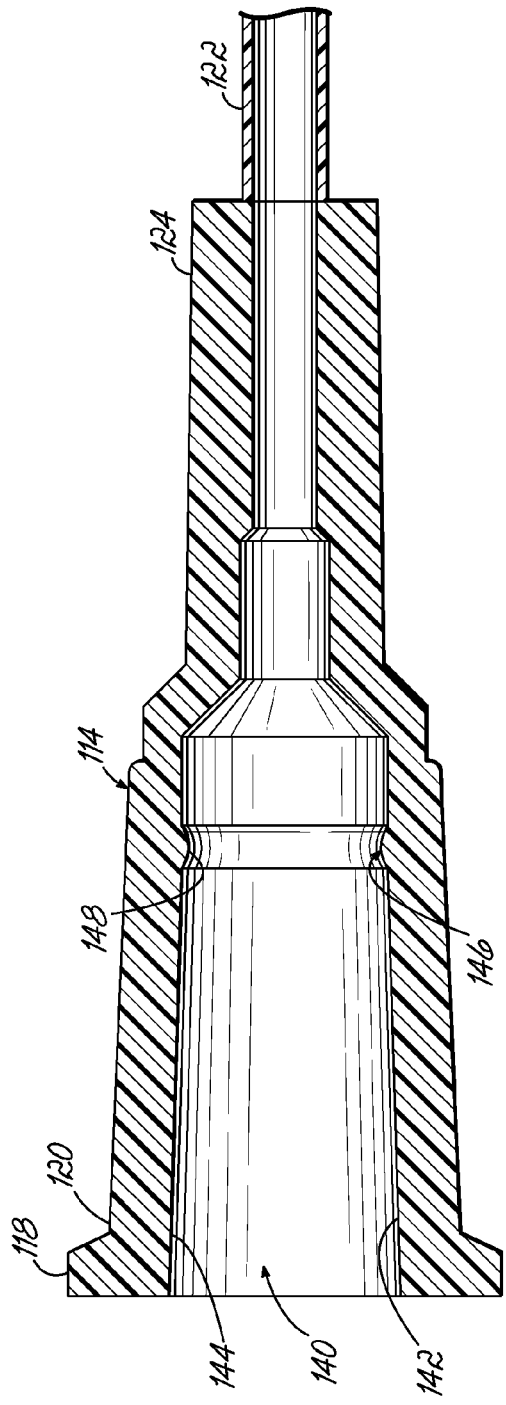
FIG. 6 is a cross-sectional view of the catheter hub of FIGS. 3A-3C for purposes of explaining the interaction of the catheter hub and the needle tip spring protector of the present invention.

With reference to FIG. 6, it will be seen that the catheter hub 114 includes an inner chamber 140 defined by an interior surface 142 having a proximal portion 144 tapered in accordance with ISO or other applicable standards for female luers. The inner chamber 140 defines a housing-engaging element 146 for cooperating with needle tip spring protector 102. In the illustrated embodiment, the housing-engaging element 146 is a generally annular protrusion 148 extending radially inward from interior surface 142 into inner chamber 140. Annular protrusion 148 is generally distal of luer tapered proximal portion 144 so as not to interfere with male luer taper connections to catheter hub 114. The protrusion 148 may, for example, be formed from an annular lip that extends along the entire inside circumference of the inner chamber 140. In alternate embodiments, the housing-engaging element 146 may include a plurality of protrusions, a groove, a plurality of grooves, or an annular groove that extends about the inside circumference of the inner chamber 140.

Annular protrusion 148 and detents 128 cooperate to hold needle tip spring protector 102 to catheter hub 114 in the extended position of needle 14 and allow for release thereof when needle 14 moves proximally towards the retracted position. In this regard, and with further reference to FIG. 7, it will be seen that in the extended position of the needle 14, the shaft 22 thereof is in passage 112, thus limiting the ability of second resilient arm 110 to compress (i.e., to flex radially inwardly). At the same time, detents 128 define an outer diameter of annular ring 134 that is slightly greater than the inner diameter of annular protrusion 148, and which may closely correspond to the inner diameter of catheter hub interior surface 142 just distal of annular protrusion 148. Thus, with needle shaft 22 in the extended position, as seen in FIG. 7, detents 128 provide a generally rigid hold to catheter hub 114 by cooperating with the distal-facing surface of annular protrusion 148.

Figure 7:
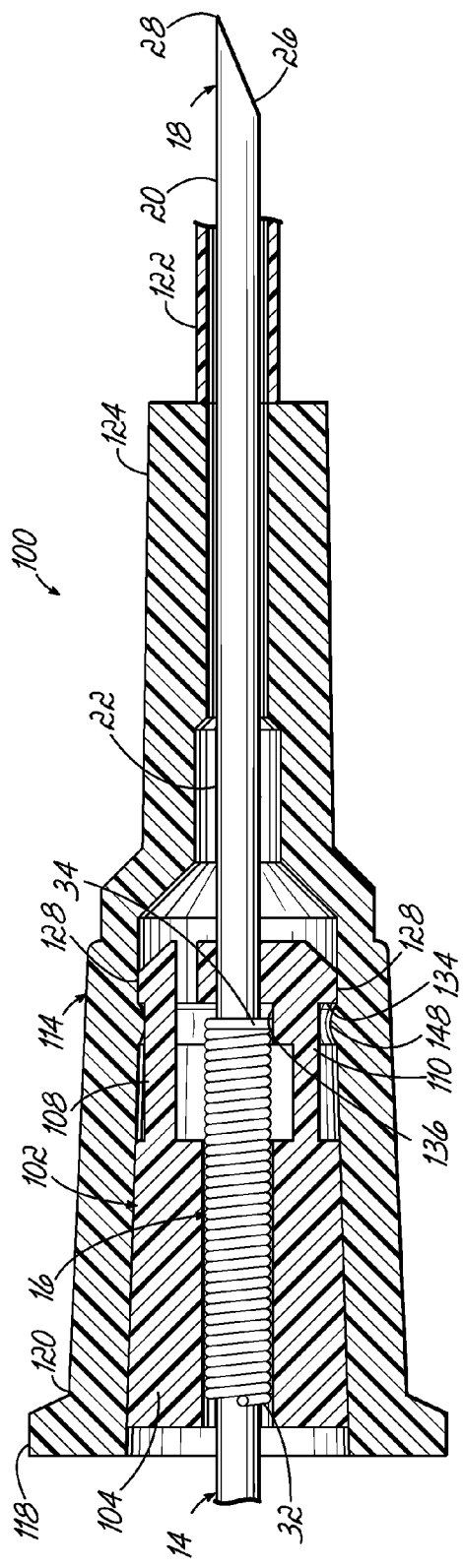
FIG. 7 is a cross-sectional view of the assembled catheter assembly of FIGS. 3A-3C, wherein the needle is in an extended position and the spring is in an armed state.
Figure 8:
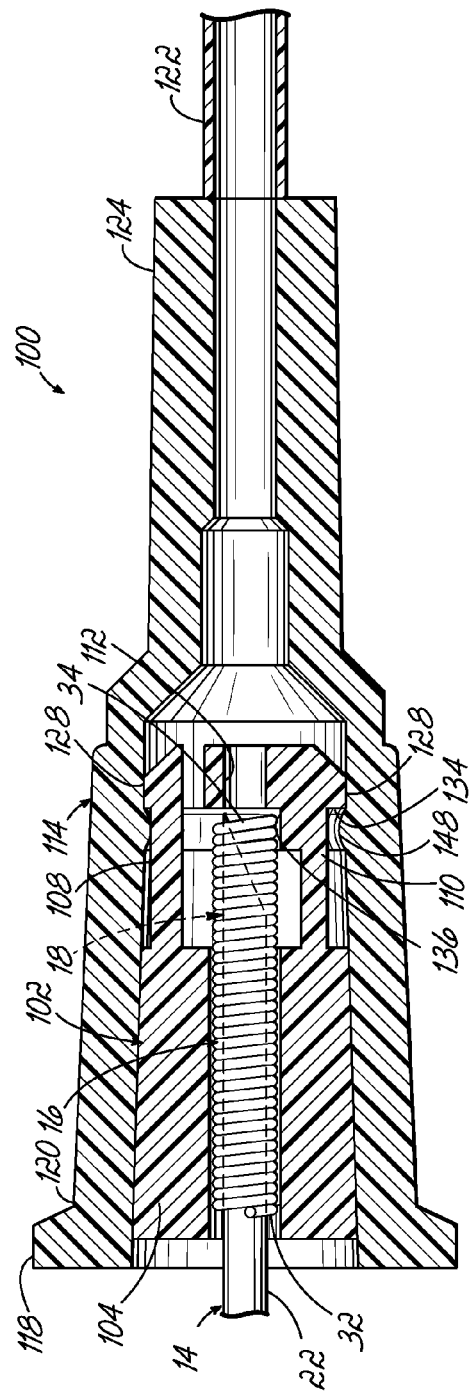
FIG. 8 is a cross-sectional view of the catheter assembly of FIGS. 3A-3C with the needle moved to a retracted position and the spring in an activated state.

In FIG. 7, the proximal end 32 of the spring 16 is held in place (e.g., channel 138) while the spring 16 is in an armed state with its distal end 34 restrained against the bearing surface 136. In this configuration, the needle 14 is allowed to freely move through the housing 104, the spring 16, the catheter hub 114, and the catheter tube 122. Moreover, with the needle 14 in the extended position, detents 128 are seated distal of annular protrusion 148 in catheter hub 114 with a light frictional fit that allows the healthcare worker (not shown) to rotate catheter hub 114 relative to needle tip spring protector 102. Thus, initially the needle tip spring protector 102 is fixedly engaged with the catheter hub 114 in FIG. 7 such that any forces resulting from proximal movement of the needle 14 (e.g., via proximal movement of needle hub 116 by a healthcare worker) are insufficient to release the needle tip spring protector 102 from the catheter hub 114. However, once the spring 16 activates so as to grippingly engage the shaft 22 of the needle 14 (as shown in FIG. 8), the needle tip spring protector 102 and needle 14 are effectively secured together such that the proximal movement of needle 14 generates a force sufficient to overcome the holding force of housing 104 to catheter hub 114. More particularly, with the needle 14 out of the way, the first and second resilient arms 108, 110 are allowed to flex and move past the protrusion 148 and allow the needle tip spring protector 102 to release from the catheter hub 114. Thus, it is not until needle shaft 22 is effectively proximally beyond passage 112, such as with tip 18 protected by needle tip spring protector 102 in the retracted position of needle 14, as seen in FIG. 8, that either or both of first and second resilient arms 108, 110 are flexed. As a consequence, continued proximal pulling on needle hub 116 causes one or both of resilient arms 108, 110 to flex enough that detents 128 move proximally of annular protrusion 148, and then to flex or expand back to the nominal position.

To move to the gripping state in the retracted position of the needle, the spring 16 may move out of contact with bearing surface 136 by alternate mechanisms. For example, with reference to FIGS. 7-11B, when the needle 14 is in the extended position, the needle 14 and spring 16 are in substantial coaxial alignment. The spring 16 is prevented from moving out of substantial coaxial alignment due to the presence of the needle 14 within the passage 30 of the spring 16. As the needle 14 is retracted, the distal end 20 of the needle 14 will move to a point that allows at least a segment of the spring 16, such as the distal end 34, to move relative to the needle 14. For example, as in FIG. 9A, the needle 14 has been retracted such that its distal tip 18 is within the passage 112 of the second resilient arm 110. The spring 16 is in an armed state with its distal end 34 constrained against a bearing surface 136 of the second resilient arm 110 of the housing 104. As can be seen from the view of FIG. 9B, the distal end 34 of the spring 16 terminates in a relatively flat surface 154 that sits on a relatively flat bearing surface 136. The rotational bias of the spring 16 urges the distal end 34 in a counter-clockwise direction in this example. One of ordinary skill will recognize that the distal end 34 could also be positioned to account for a clockwise rotating spring 16.

In order for the distal end 34 to rotate, though, the spring 16 would have to flex upwardly so that the distal end 34 can slip past the bearing surface 136. Such upward flexing is prevented, however, by the presence of the needle 14. As the spring 16 attempts to flex upwardly, it is stopped when the inner surface 38 contacts the shaft 22 of needle 14. In such a configuration, the needle 14 and spring 16 are in substantial coaxial alignment. In FIG. 10A, the needle 14 is withdrawn to a point where a portion of the needle tip 18, for example region 26, is proximal of the distal end 34 of the spring 16. Because the tip 18 of the needle 14 does not entirely restrain the distal end 34 of the spring 16 in this position, the distal end 34 is able to flex such that it can escape the restraint provided by the bearing surface 136 and can begin rotation in the counter-clockwise direction, as shown in FIG. 10B. Thus, the passing of a portion of the tip 18 of the needle 14 past the distal end 34 of the spring 16 allows at least a portion of the spring 16 to move out of substantial coaxial alignment with the needle 14 to activate the release of the spring 16 to the gripping state. However, it will be recognized that in alternate embodiments, a portion of the spring 16 need not move out of substantial coaxial alignment with needle 14 to release spring 16 from bearing surface 136. For example, if a bearing surface 136 were on the needle 14 rather than on the housing 104, region 26 of needle 14 can provide space for spring 16 to release from bearing surface 136 without the spring 16 moving out of substantial coaxial alignment with needle 14. It will also be recognized, that although FIG. 10B is drawn with region 26 downwards towards bearing 136, thus allowing spring 16 to begin to deflect upwardly as soon as region 26 enters spring 16, activation would still occur even if region 26 were oriented upwards, or at any other orientation, although activation may be delayed until sharp point 28 is fully within spring 16.

FIGS. 11A and 11B illustrate the spring 16 after it has been activated and grippingly engages the shaft 22 of the needle 14. The spring 16 is restrained within the needle tip spring protector 102 via its proximal end 32. Thus, movement of the needle 14 will be directly transferred to the needle tip spring protector 102 through the engagement of the spring 16 with the needle 14. Further, with the needle 14 removed from the passage 112, the second resilient arm 110 is free to flex inwardly. The first resilient arm 108 is also free to flex inwardly and thus, the resilient arms 108, 110 can flex past the annular protrusion 148 to allow the needle tip spring protector 102 to release from the catheter hub 114. Thus, the normal activity of retracting the needle hub 116 from the catheter hub 114 activates the needle tip spring protector 102 without any additional action by the healthcare worker, and further retraction of the needle hub 116, after activation, releases the needle tip spring protector 102 from the catheter hub 114 without additional manipulation by the healthcare worker.

Figure 12A:
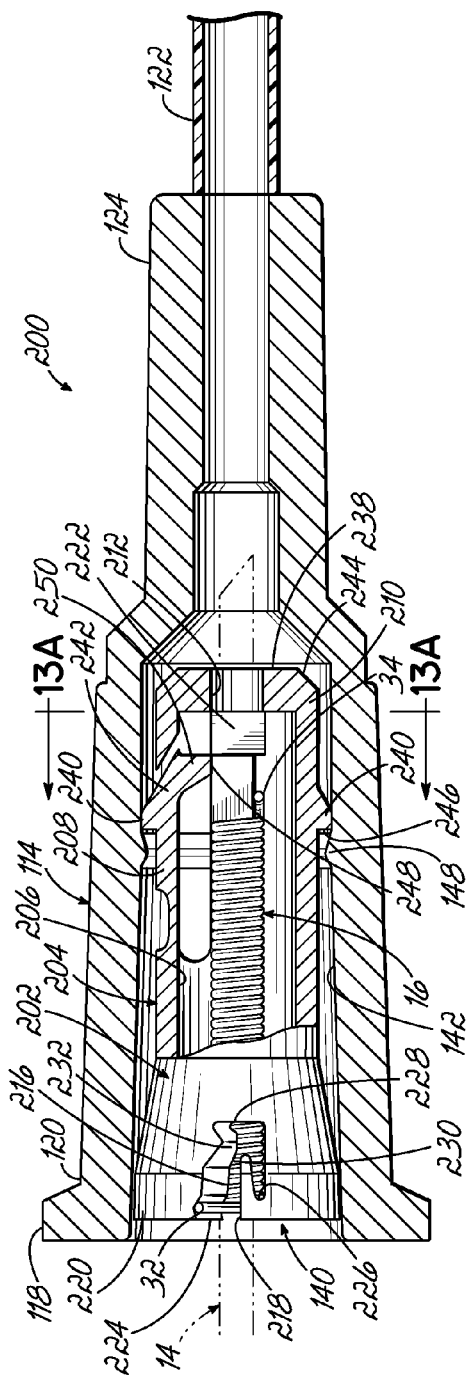
FIG. 12A is a cross-sectional elevational view of a catheter assembly depicting a third embodiment of a needle tip spring protector in accordance with the principles of the present invention, prior to introducing a needle, and with the spring wound and in a first axial position.
Figure 12B:
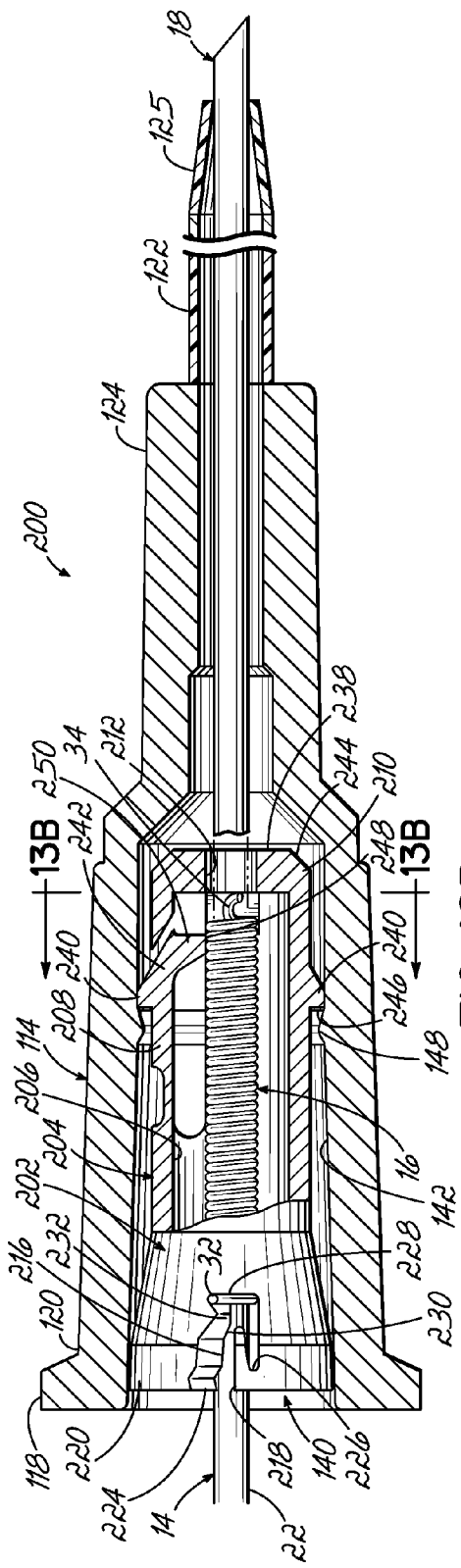
FIG. 12B is a cross-sectional elevational view of the catheter assembly of FIG. 12A after introducing a needle, and with the spring in a second axial position.

With reference to FIGS. 12A-12F, there is shown catheter assembly 200, which may be essentially the same as catheter assembly 100 described above, but including a third embodiment of a needle tip spring protector 202. Needle tip spring protector 202 may include essentially the same spring 16 as in the first and second embodiments. Needle tip spring protector 202 includes a housing 204 having a passage 206 for receiving needle 14 therethrough, and first and second resilient arms 208, 210 wherein at least one arm defines a passage 212 generally axially aligned with passage 206. FIG. 12A depicts the catheter assembly 200 prior to introduction of needle 14 to the assembly. FIG. 12B depicts the catheter assembly 200 as an assembled unit with needle 14 introduced to the assembly. FIGS. 12C-12F depict the operation of the needle tip spring protector 202, and the relative positions of catheter hub 114 and needle tip spring protector 202 during use.

The catheter assembly 200 includes a needle hub 116 (FIG. 3B) with needle 14 extending therefrom. Catheter hub 114 of catheter assembly 200 includes luer fitting 118 on its proximal end and catheter tube 122 extending distally from the distal end 124 of the catheter hub 114. Needle shaft 22 extends through housing 204, spring 16, catheter hub 114, and catheter tube 122 with an exposed tip 18 exiting the distal end 125 of the catheter tube 122 in an extended position of the needle 14 (as shown in FIG. 12B).

The spring 16 has a first axial position and a second axial position relative to housing 204. In FIG. 12A, the spring 16 is shown in the first axial position prior to insertion of the needle 14 into the catheter assembly 200. FIG. 12B depicts the spring 16 after having been moved to the second axial position, with the needle 14 inserted through the needle tip spring protector 202. The spring 16 may be moved from the first axial position to the second axial position by using a separate tool (not shown) to push the spring 16 in a distal direction. In such an embodiment, the spring 16 is in an armed state in the first axial position, and remains in an armed state when moved to the second axial position. An armed state in the first axial position is obtained by winding the spring 16 by holding the distal end 34 of the spring 16 against its rotational bias and in contact with a ledge 213 defined by an inner surface 214 of housing 204, and holding the proximal end 32 against its rotational bias and in contact with a tool (not shown) outside of the housing 204. Once wound, the spring 16 is moved slightly distally so that proximal end 32 is placed on a contour 216 of a notch 218 in a proximal end 220 of the housing 204 as seen in FIG. 12A.

Figure 13A:
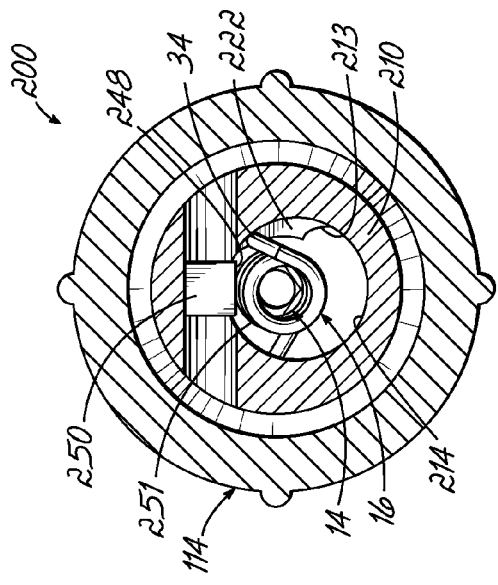
FIGS. 13A-13D are cross-sectional views of the needle tip spring protector of FIGS. 12A-12D taken along lines 13A-13A of FIG. 12A, 13B-13B of FIG. 12B, 13C-13C of FIG. 12C, and 13D-13D of FIG. 12D.
Figure 13B:
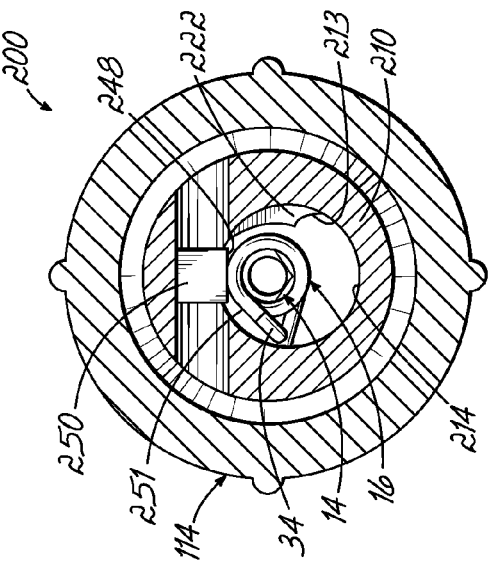
Figure 13C:
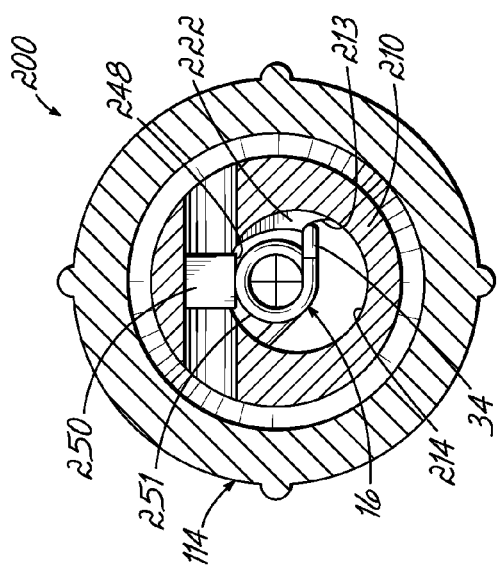

As the spring 16 moves from the first axial position of FIG. 12A to the second axial position of FIG. 12B, the distal end 34 of the spring 16 remains in contact with the ledge 213 until it is moved onto a bearing surface 222 (refer to FIGS. 12A and 13A), and therefore does not rotate in the direction of the rotational bias of the spring 16. Although not shown in FIG. 12B, but as can be seen in FIGS. 13A-13B, when moved to the second axial position, the distal end 34 of the spring 16 moves out of contact with the ledge 213 of the housing 204 to be received against the bearing surface 222 of the housing 204.

Further, as the spring 16 moves from the first axial position to the second axial position, the proximal end 32 of the spring 16 moves distally along the contour 216 of the notch 218. The notch 218 of the illustrated embodiment is in a general U or V shape with an open end 224 and a closed end 226. However, it will be recognized by those skilled in the art that a U or V shape is not necessary, and any shape may be used that serves the principles of the present invention. When the spring 16 reaches the second axial position, the proximal end 32 is located at a distal portion 228 of the notch 218. Prior to being received at the distal portion 228, the proximal end 32 passes through a narrowed portion 230 formed by a protrusion 232. The narrowed portion 230 is shaped such that it will allow passage of the proximal end 32 in a direction from the open end 224 to the distal portion 228, but will prevent passage of the proximal end 32 in a direction from the distal portion 228 to the open end 224. Since the proximal end 32 of the spring 16 is received on a distal side of protrusion 232, the rotational bias of the spring 16 will keep the proximal end 32 in the distal portion 228 while spring 16 is in the armed state.

The distal end 238 of the housing 204 includes first resilient arm 208 and second resilient arm 210. The second resilient arm 210 includes a passage 212 generally axially aligned with passage 206. At least one arm, and as in the illustrated embodiment, both of arms 208, 210, include a detent 240 at distal ends 242, 244, respectively, to define segments of an annular ring 246. These first and second resilient arms 208, 210 interact with features of the catheter hub 114, as explained below, to control the release of the needle tip spring protector 202 from the catheter hub 114.

Further, as can be seen in FIGS. 12A-12F, first resilient arm 208 has a surface 248, which may be provided by a leg 250, that contacts and confronts the outer surface 251 of the spring 16 when the spring 16 is in the second axial position. In the illustrated embodiment, leg 250 is located at a distal end 242 of the first resilient arm 208. However, this location is merely exemplary. Further, any surface of first resilient arm 208 may be used to contact spring 16, and thus does not necessarily require a downwardly-depending protrusion, such as leg 250. It can further be seen from the figures that first resilient arm 208 is disposed proximally of the distal end 238 of the housing 204.

With the spring 16 in the second axial position, and the needle 14 in the extended position, detents 240 are seated distal of annular protrusion 148 in catheter hub 114 with a light frictional fit that allows the healthcare worker (not shown) to rotate catheter hub 114 relative to needle tip spring protector 202. Thus, initially the needle tip spring protector 202 is fixedly engaged with the catheter hub 114 (as in FIG. 12B) such that any forces resulting from proximal movement of the needle 14 (e.g., via proximal movement of needle hub 116 by a healthcare worker) are insufficient to release the needle tip spring protector 202 from the catheter hub 114. However, once the needle tip spring protector 202 activates, such that spring 16 grippingly engages the shaft 22 of the needle 14 (FIG. 12D), the needle tip spring protector 202 and needle 14 are effectively secured together such that the proximal movement of needle 14 generates a force sufficient to overcome the holding force of housing 204 to catheter hub 114. More particularly, with needle 14 out of the way, the first and second resilient arms 208, 210 are allowed to flex and move past the protrusion 148 and allow the needle tip spring protector 202 to release from the catheter hub 114. Thus, it is not until needle shaft 22 is effectively proximally beyond passage 212, such as with tip 18 protected by needle tip spring protector 202 in the retracted position of needle 14, that either or both of first and second resilient arms 208, 210 are flexed. As a consequence, continued proximal pulling on needle hub 116 causes one or both of resilient arms 208, 210 to flex enough that detents 240 move proximally of annular protrusion 148 while the surface 248 of leg 250 moves into the space formerly occupied by the spring 16 (FIG. 12E), and then to flex or expand back to the nominal position (FIG. 12F).

As the spring 16 moves from the second axial position back toward the first axial position and to a third axial position (which may be at or near the first axial position), the outer surface 251 of the spring 16 is moved proximally and out of contact with the leg 250. This provides space for the first resilient arm 208 to flex to release the housing 204 from the interior of the catheter hub 114. As will be appreciated by those of skill in the art, the positioning of the spring 16 in contact with the leg 250 in the second axial position prevents the housing 204 from releasing from the catheter hub 114 until the spring 16 has moved to the gripping state to grip the needle 14. This ensures that the housing 204 cannot be removed from the catheter hub 114 until the needle tip 18 is protected.

With the needle 14 removed from the passage 212, the second resilient arm 210 is free to flex, and thus can move away from protrusion 148 to allow the needle tip spring protector 202 to release from the catheter hub 114, as described above. It will be recognized by those skilled in the art that the second resilient arm 210 need not be received distally of a protrusion 148, but may engage other housing-engaging elements 146, such as a plurality of protrusions, a groove, a plurality of grooves, or an annular groove.

Figure 13D:
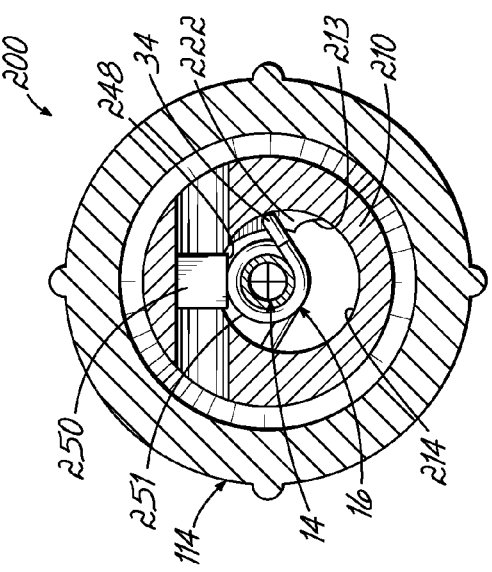

In operation, catheter assembly 200 is inserted into a patient and, while the catheter hub 114 is held steady, the needle hub 116 and needle 14 can be retracted to withdraw the needle 14 from the patient (as shown in FIGS. 12C-12F). As the needle 14 is retracted (i.e., withdrawn proximally), the needle tip 18 will pass through the passage 212 towards the spring 16. As shown in FIG. 12C, the distal end 18 of the needle 14 will move to a point that allows at least a segment of the spring 16, such as the distal end 34, to move relative to the needle 14. In particular, the region 26 of the needle 14 will move to a position adjacent distal end 34 of spring 16. Region 26 provides space for the distal end 34 of spring 16 to move away from bearing surface 222 and to then rotate in the direction of the rotational bias of spring 16. As a result of the spring 16 rotating in this manner, the inner diameter 36 of the spring 16 is reduced to the gripping state so that it grippingly engages the shaft 22, as shown in FIGS. 12D and 13D.

Once the spring 16 grippingly engages the needle 14 continued retraction of the needle 14 will result in the configuration of FIGS. 12E and 12F, in which the needle tip spring protector 202 disengages from the inside of the catheter hub 114 while surrounding tip 18 of needle 14. As the needle 14 is retracted, proximal end 32 of spring 16 will cooperatively move from distal portion 228 of notch 218 (second axial position) to closed end 226 of notch 218 (third axial position). Contact of the proximal end 32 of spring 16 with closed end 226 provides the force, upon continued retraction of needle 14, to withdraw needle tip spring protector 202 from catheter hub 114.

Thus, in operation, the needle tip spring protector 202 engages the inside of the catheter hub 114 with a holding force greater than the force that the needle 14 may exert on the needle tip spring protector 202 while the needle 14 is being retracted. As a result, the needle tip spring protector 202 remains attached to the catheter hub 114 while the needle hub 116 and needle 14 are being retracted to withdraw the needle 14 from the patient. However, when the needle tip spring protector 202 activates so as to grip the shaft 22 of the needle 14, the gripping force is greater than the holding force between the catheter hub 114 and the needle tip spring protector 202. Thus, when the needle 14 continues to be retracted after the needle tip spring protector 202 has activated, the needle tip spring protector 202 is released from the catheter hub 114 and remains in position covering the tip 18 of the needle 14.

Thus, this embodiment of the present invention provides a passive release of the needle tip spring protector 202 from the catheter hub 114. The normal activity of retracting the needle hub 116 from the catheter hub 114 activates the needle tip spring protector 202 without any additional action by the healthcare worker. Moreover, further retraction of the needle hub, releases the needle tip spring protector 202 from the catheter hub 114 without additional manipulation by the healthcare worker. As a result, the present invention provides a needle tip spring protector 202 for a catheter assembly 200 that includes both passive activation and passive release.

Figure 14:
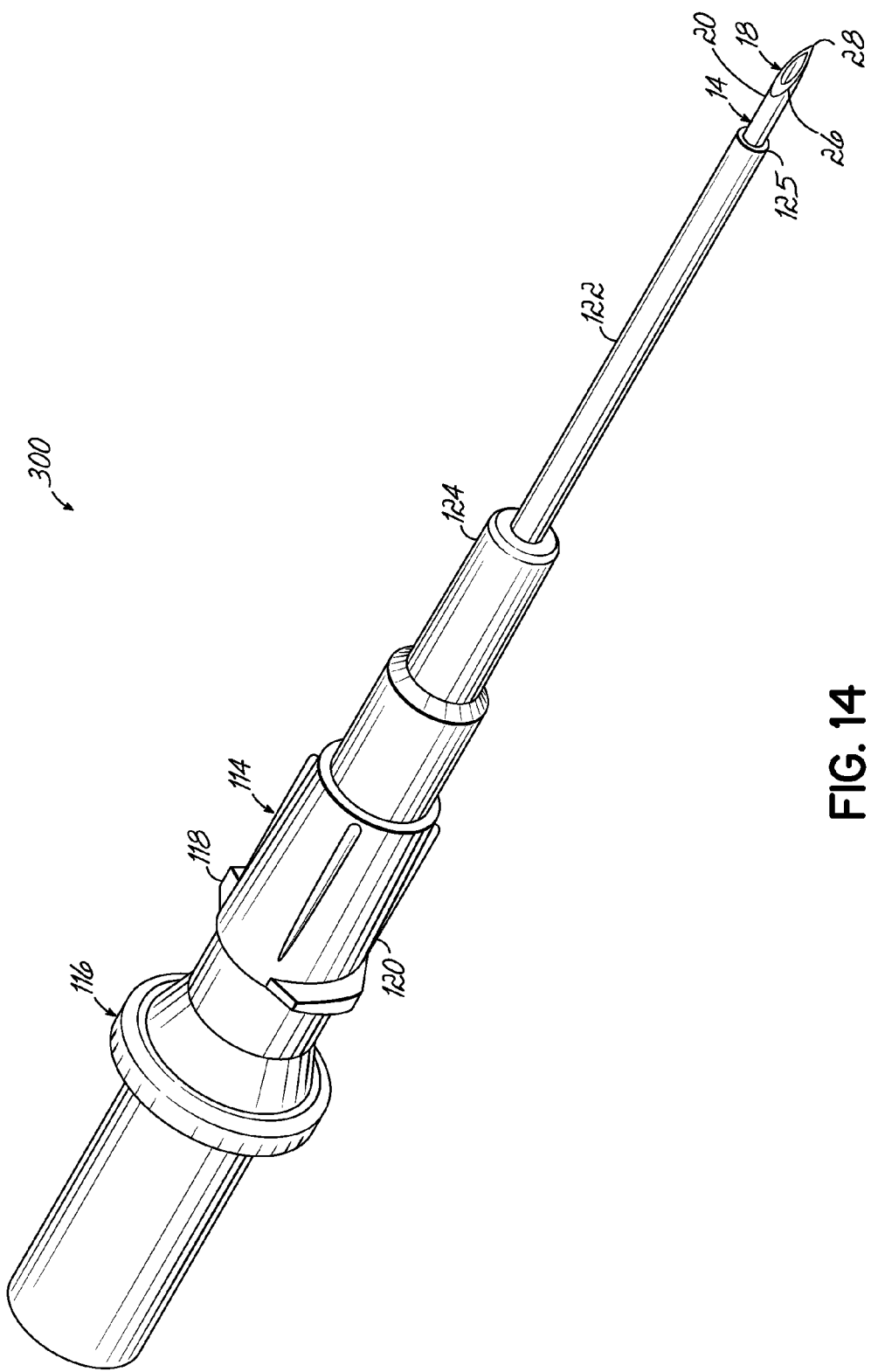
FIG. 14 is a perspective view of a catheter assembly including a fourth embodiment (not visible) of a needle tip spring protector in accordance with the principles of the present invention.
Figure 15:
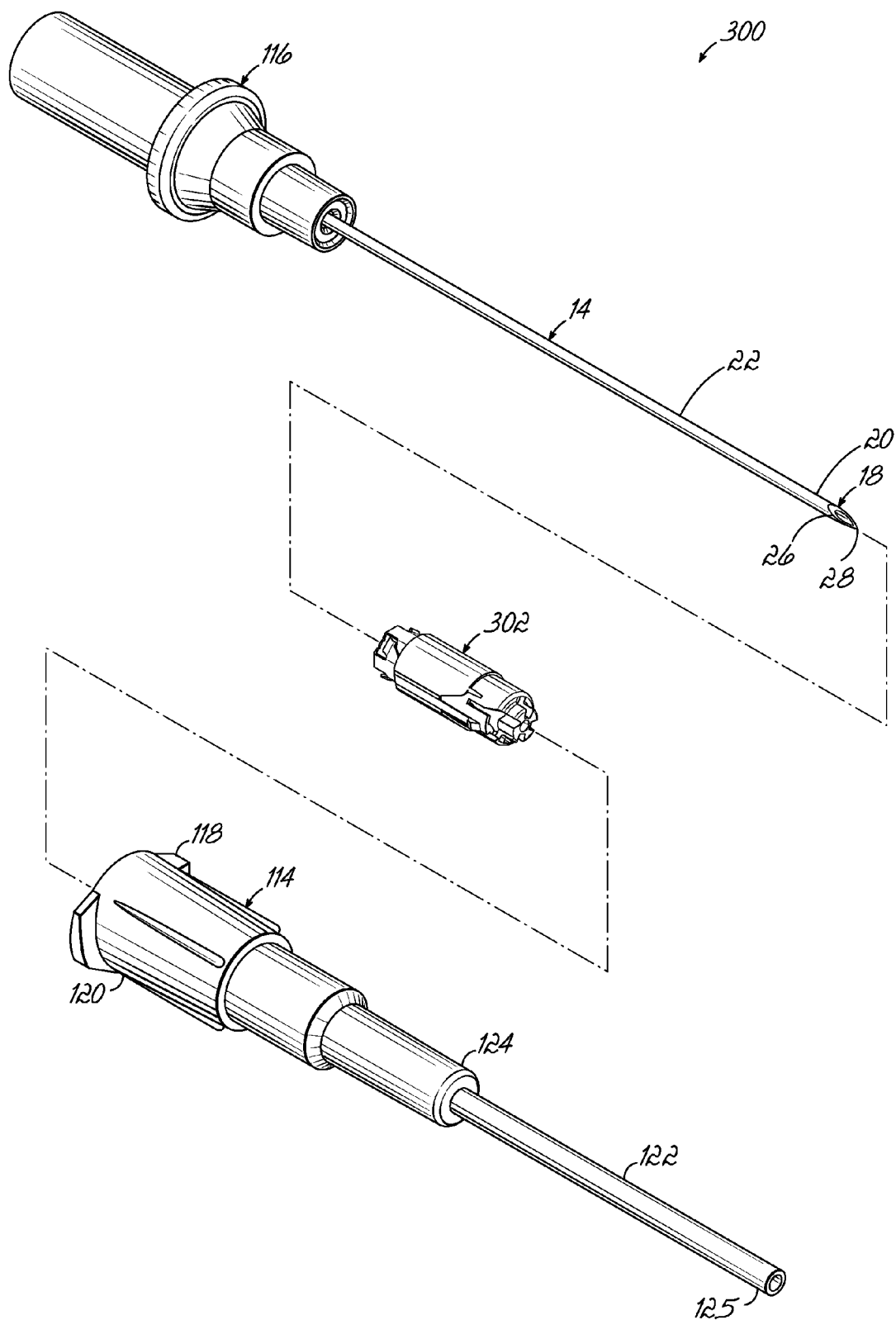
FIG. 15 is an exploded view of the catheter assembly of FIG. 14, with the needle tip spring protector in the pre-armed state.

A fourth embodiment of a needle tip spring protector is described with reference to FIGS. 14-22A. This embodiment includes certain features to enhance manufacturability, as well as to further secure the needle tip spring protector onto the needle after it has been activated. To this end, FIGS. 14 and 15 depict a catheter assembly 300 consisting of a needle hub 116 having a needle 14 extending distally thereof, a needle tip spring protector 302, and a catheter hub 114 having catheter tube 122 extending distally thereof. When assembled, the needle 14 extends through the needle tip spring protector 302 and passes through the catheter tube 122 so that the tip 18 is protruding beyond the distal end 125 of the catheter tube 122. The needle tip spring protector 302 is disposed in the catheter hub 114 and is adapted to protect the tip 18 of needle 14 when the needle 16 is withdrawn.

Figure 16:
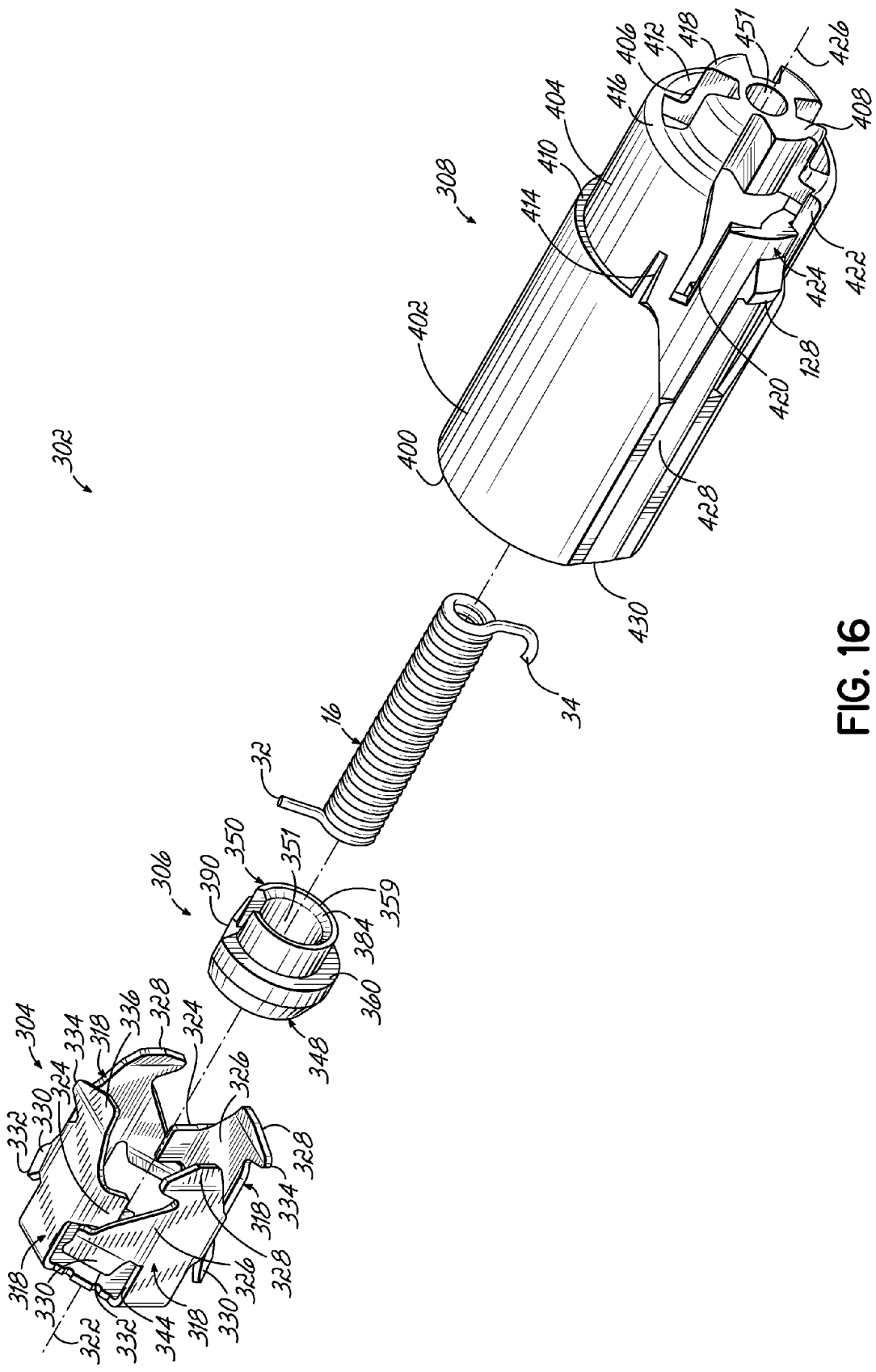
FIG. 16 is an exploded view of the needle tip spring protector of FIG. 15.
Figure 17:
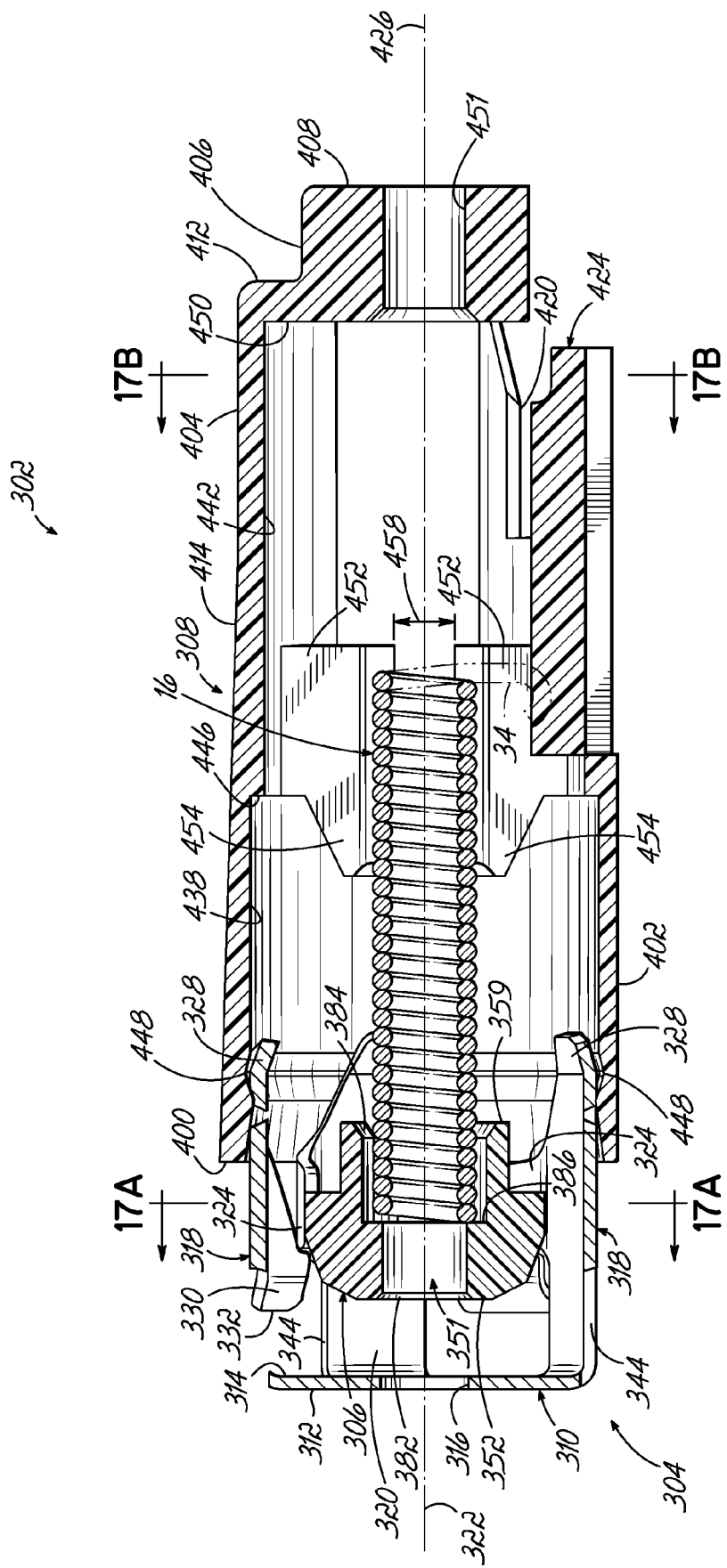
FIG. 17 is an elevational side view cross-section of the needle tip spring protector of FIG. 14 in the assembled state, prior to pre-arming.

The details of the needle tip spring protector 302 are illustrated in FIGS. 16-17A and include a cup 304, a washer 306, a spring 16, and a housing 308 that collectively cooperate to perform a tip protection function of needle 14. The cup 304 has a base 310 with a proximal face 312, a distal face 314 and an aperture 316 through base 310 and extending between proximal and distal faces 312, 314. The aperture 316 is sized to receive the shaft 22 of needle 14 therethrough. Four arms 318 extend distally from the base 310 and define an inner chamber 320. A center axis 322 of the cup 304 is defined as being through the center of aperture 316, generally perpendicular to the base 310, and approximately in-line with the center of the four arms 318. When not installed in the housing 308, the angle between the base 310 and the arms 318 is greater than 90 degrees, and preferably approximately 95 degrees, resulting in a slight flaring of the arms 318 in a radially outward direction. Each arm 318 has an interior tab 324, an exterior tab 326 on opposite sides of the arm 318, and a distal tab 328 opposite the base 310. The interior tabs 324 and exterior tabs 326 have an overlapping relationship and define at least in part inner chamber 320. More particularly, the inner tab 324 of one arm 318 is nearer to, but does not contact, the exterior tab 326 of the neighboring arm 318. This arrangement allows the four arms 318 to be squeezed or flexed inwardly, changing the angle relative to the base 310 from approximately 95 degrees, to a smaller angle such as approximately 90 degrees, before the interior and exterior tabs 324, 326 come into contact with one another.

The exterior tab 326 has a proximal tab portion 330 that is angled radially outwardly from the center axis 322 of the cup 304, terminating at a locking edge 332. Each of the distal tabs 328 has a circumferentially extending nose that defines a locking point 334 at the end thereof. Each of the distal tabs 326 has an insertion portion 336 that is angled toward the center axis 322 to aid in the entry of the four arms 318 into the proximal end of the housing 308 during assembly. One of the four interior tabs 324 (FIG. 17A) is an arming tab 338 which is longer than the other three interior tabs 324 and has a generally V-shaped notch 340 formed therein. A semicircular cutout 342 in the edge of the base 310 provides an optional visual and tactile reference for the location of the arming tab 338. Opposing windows 344 are defined between neighboring arms 318 and adjacent base 310 make it possible to pass objects through the inner chamber 320. As described below, the windows 344 may be used during assembly of the needle tip spring protector 302. The base 310 may further include one or more cutouts 346 used in the manufacturing and/or assembly of the tip protector 302.

Figure 16A:
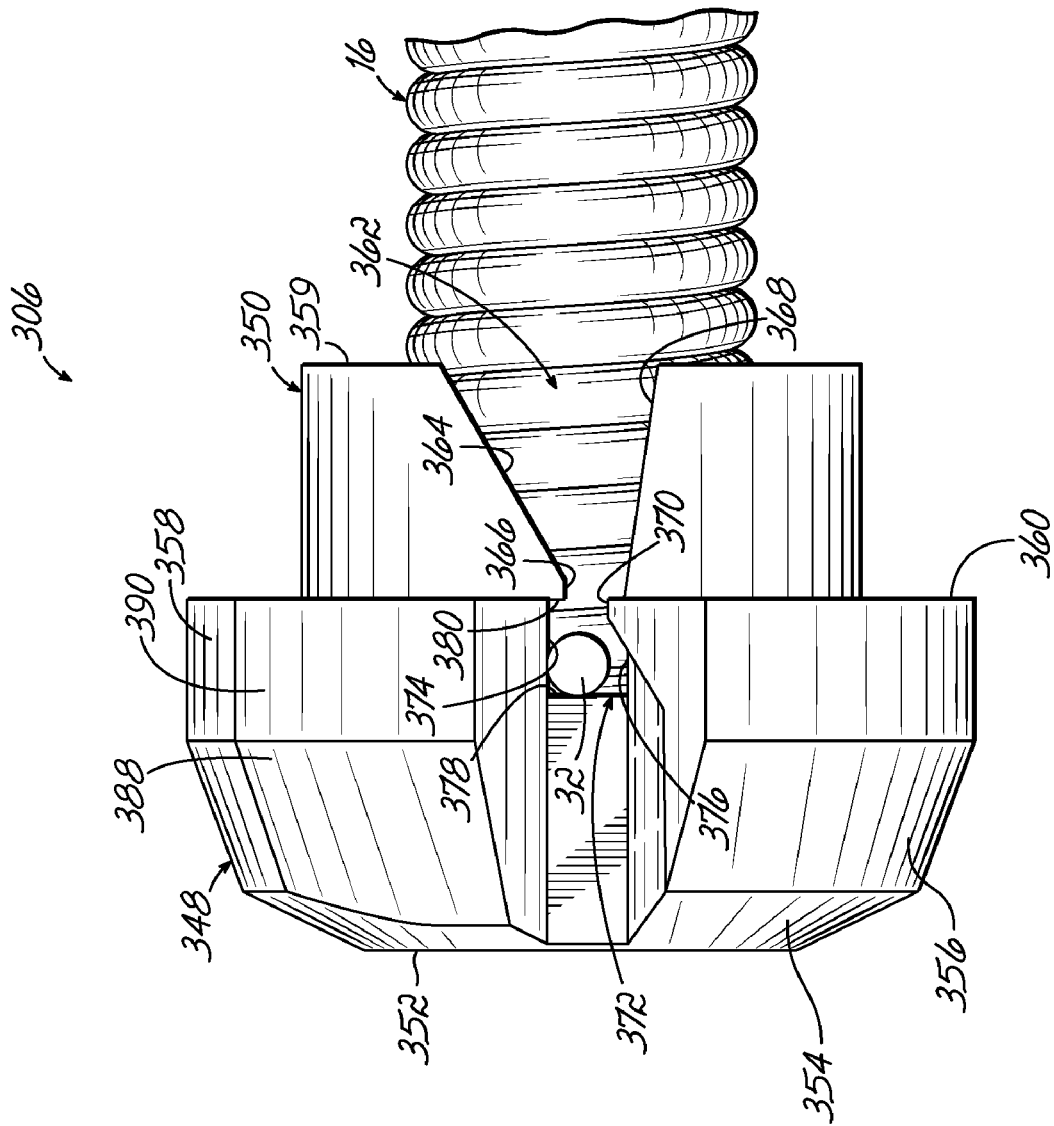
FIG. 16A is a partial detail view of the spring and washer of FIG. 15 locked together.

As shown in FIGS. 16 and 16A, the washer 306 has a head 348, a stem 350 extending distally thereof, and a passage 351 extending through washer 306. The head 348 includes a proximal face 352, a first chamfer 354, a second chamfer 356, and a generally cylindrical portion 358. The stem 350 is generally cylindrical, terminates at a distal face 359, and has a cross-dimension less than a cross-dimension of the cylindrical portion 358 of head 348 to define a distally facing shoulder 360. Further, the washer 306 includes a slot 362 extending generally in a proximal-distal direction and open along the outer periphery of the washer 306. The portion of slot 362 in stem 350 includes a first lead 364 that defines a first corner 366 and a second lead 368 that defines a second corner 370. The washer slot 362 is in communication with a spring pocket 372 that defines a first stop surface 374, a second stop surface 376, a proximal stop surface 378 and a distal stop surface 380. The spring pocket 372 is adapted to receive the proximal end 32 of spring 16 therein. Passage 351 may include proximal and distal chamfers 382, 384 adjacent proximal and distal faces 352, 359, respectively. The passage 351 has a stepped configuration to define a distally facing shoulder 386 therein. For purposes described below, the second chamfer 356 of head 348 includes an entry portion 388 and the cylindrical portion 358 of head 348 includes an entry flat 390.

Figure 18:
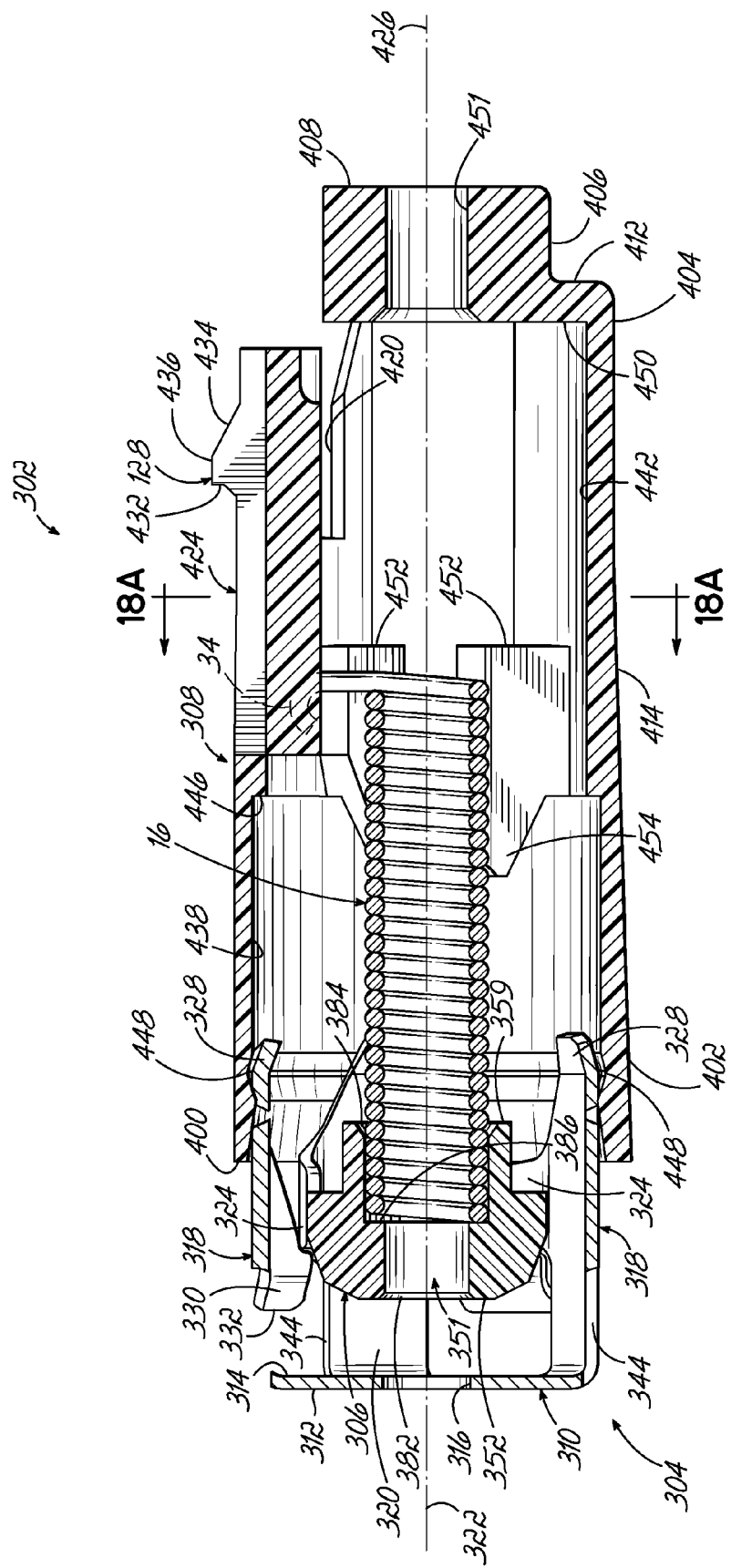
FIG. 18 is an elevational side view of the needle tip spring protector of FIG. 14 in the pre-armed state, cross-sectioned at an angle that shows the flexible arm protrusion.

The housing 308 includes a proximal face 400, a proximal portion 402, an intermediate portion 404, a distal portion 406, and a distal face 408. The portions of housing 308 have a stepped configuration to define a first distally facing shoulder 410 between proximal portion 402 and intermediate portion 404 and a second distally facing shoulder 412 between intermediate portion 404 and distal portion 406. Housing 308 may also include one or more ramp gussets 414 between proximal portion 402 and intermediate portion 404. Housing 308 may further include one or more chamfers such as chamfers 416, 418 between the various portions or between a portion and a respective face. Housing 308 further includes first and second interconnected gaps 420, 422 to define a resilient arm 424. The resilient arm 424 is substantially flat on the side facing away from a center axis 426 of the housing 308. The flat surface 428 continues proximally across the proximal portion 402 to the proximal face 400 where it defines a large flat 430. The resilient arm 424 has a detent 128 that creates a segment of an annular ring 432 and further comprises a lead 434 and a flat 436 (FIG. 18).

Interior features of the housing 308 include a proximal cavity 438 having a first diameter and a distal cavity 442 having a second reduced diameter to define a shoulder 446 between the two cavities. The proximal cavity 438 has an annular groove 448 formed therein and adjacent proximal face 400. The distal cavity 442 is bounded at the distal end thereof by an inner face 450 of distal portion 406. Additionally, distal portion 406 includes a passage 451 therethrough in communication with distal cavity 442 and is sized to receive the shaft 22 of needle 14 therethrough. The interior of housing 308 further includes a plurality (e.g., four) circumferentially spaced ribs 452 (FIG. 17B). The ribs 452 have proximally extending rib leads 454 and curved inner surfaces 456 that form an effective discontinuous rib diameter 458. The rib 452 that is adjacent to the resilient arm 424 and to the distal end 34 of spring 16 has a rib relief 460. Furthermore, the resilient arm 424 has a bearing surface 462 that defines a pre-arm portion 464 (FIG. 17B) and an arming portion 466 that is distal of the pre-arm portion 464.

The interconnectability of the various components of housing 308 will now be described. This includes, for example, placing the needle tip spring protector 302 in a pre-arm state and an armed state. Additionally, assembling a catheter assembly 300 including the needle tip spring protector 302 will also be described. In regard to assembling the needle tip spring protector 302, the cup 304 is placed base down over a first tooling pin (not shown) that passes through the aperture 316 in the base 310. Two other tooling pins (not shown) are passed through opposing windows 344 in the cup 304 to lie substantially horizontal on either side of and generally perpendicular to the first tooling pin. The washer 306, proximal face down (FIG. 17), is aligned so that the entry flat 390 and entry portion 388 align with the arming tab 338 of cup 304 as shown in FIG. 17A. The washer 306 is then lowered onto the first tooling pin and into the cup 304 to rest on the two horizontal pins that extend through windows 344. The horizontal pins locate the spring pocket 372 of the washer 306 in vertical alignment with the notch 340 in the arming tab 338. The spring 16 is placed over the first tooling pin, and lowered such that the proximal end 32 engages the spring slot 362 and into the spring pocket 372 of the washer 306 (FIG. 16A). Once inserted therein, movement of the proximal end 32 of spring 16 out of spring pocket 372 is restricted due to the configuration of first corner 366, second corner 370, and distal stop surface 380. Thus, the washer 306 and spring 16 become a substantially inseparable assembly with the proximal end 32 of the spring 16 positioned in spring pocket 372 and in alignment with the notch 340.

With further reference to FIG. 17, the housing 308 is circumferentially oriented so that the distal end 34 of the spring 16 will pass between the rib relief 460 and the resilient arm 424. The housing 308 is then lowered over the first tooling pin so that the ribs 452 pass over the outer surface 251 of spring 16. As the proximal face 400 of the housing 308 approaches the cup 304, the insertion portions 336 of the arms 318 enter the proximal cavity 438 of the housing 308, and the arms 318 begin to flex from their radially outward position (e.g., angled approximately 95 degrees relative to base 310) toward their radially inward position (e.g., angled approximately 90 degrees relative to the base 310). The housing 308 and cup 304 are pushed together until the locking point 334 on the distal tabs 328 enter the annular groove 448. At approximately the same time, the distal end 34 of the spring 16 reaches the pre-arm portion 464 of the bearing surface 462 on resilient arm 424. As seen in FIGS. 17 and 17B, there is some clearance between the outside surface 251 of the spring 16 and the inner surface 456 of ribs 452 while the spring 16 is in its rest state. The arms 318 of the cup 304 are flexed to their radially inward position by the housing 308 and the resiliency of the arms 318 exert a radially outward force through the locking points 334 on the inside of the housing 308 at the annular groove 448 to retain the cup 304 thereto.

Figure 18A:
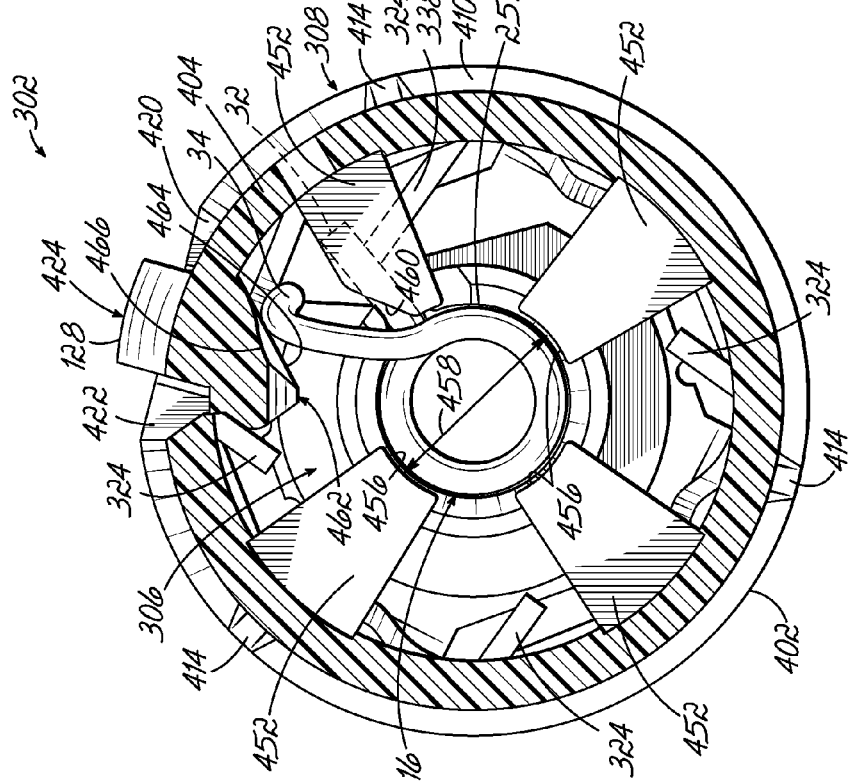
FIG. 18A is a cross-sectional view as indicated in FIG. 18.

To pre-arm the needle tip spring protector 302 (FIG. 18), the housing 308 is rotated in the direction of the arrow (FIG. 17B) relative to the cup 304, which is kept stationary by the two horizontal pins through the opposing windows 344 or by other suitable means. This rotation immediately brings the pre-arm portion 464 into contact with the distal end 34 of the spring 16, which then drives the proximal end 32 of spring 16 securely into the notch 340 on the arming tab 338 of the cup 304. Continued rotation of the housing 308, such as for example, for approximately two and one-half turns total, enlarges the spring diameter 36 as shown in FIGS. 18 and 18A. At this state, known as the pre-arm state, the needle tip spring protector 302 is stable. The housing 308 and the cup 304 are prevented from rotating relative to each other in the reverse direction by the locking points 334 engaging the annular groove 448. In other words, the circumferentially extending nose on the distal tabs 328 is configured to allow rotation of the housing 308 in a first circumferential direction but prevent rotation in the opposite circumferential direction. The washer 306 is prevented from moving toward the cup base 310 by the proximal end 32 of the spring 16 that firmly holds the washer 306 at the height of the notch 340. The distal end 34 of spring 16 will not unwind because the now enlarged outside diameter of the spring 16 has no room for movement within the effective rib diameter 458 of ribs 452. Accordingly, the distal end 34 is prevented from flexing away from or otherwise disengaging the pre-arm portion 464 of the bearing surface 462. Once in the pre-arm position, the two horizontal pins may be removed and the needle tip spring protector 302 (FIGS. 15 and 18) can be removed from all tooling and handled and stored for later assembly into a catheter assembly 300, as will now be described.

Although the above description contemplates pre-arming the needle tip spring protector 302 by rotation of housing 308 relative to cup 304, such pre-arming may also be accomplished in other ways that are contemplated to be within the scope of the invention. For example, a flat could be provided on the needle to be used to interface with a feature in the housing, and the needle could then be rotated to rotate the housing and wind the spring. However, if this were the case, it would be necessary that the spring to be pre-wound to a large enough diameter for the needle to pass through the spring to reach the interface feature, or the interface feature could instead be proximal of the spring. Thus, the spring may need to be pre-wound enough to allow the needle to pass, and then be additionally wound to give the spring more torsion to push against the resilient arm.

Figure 19A:
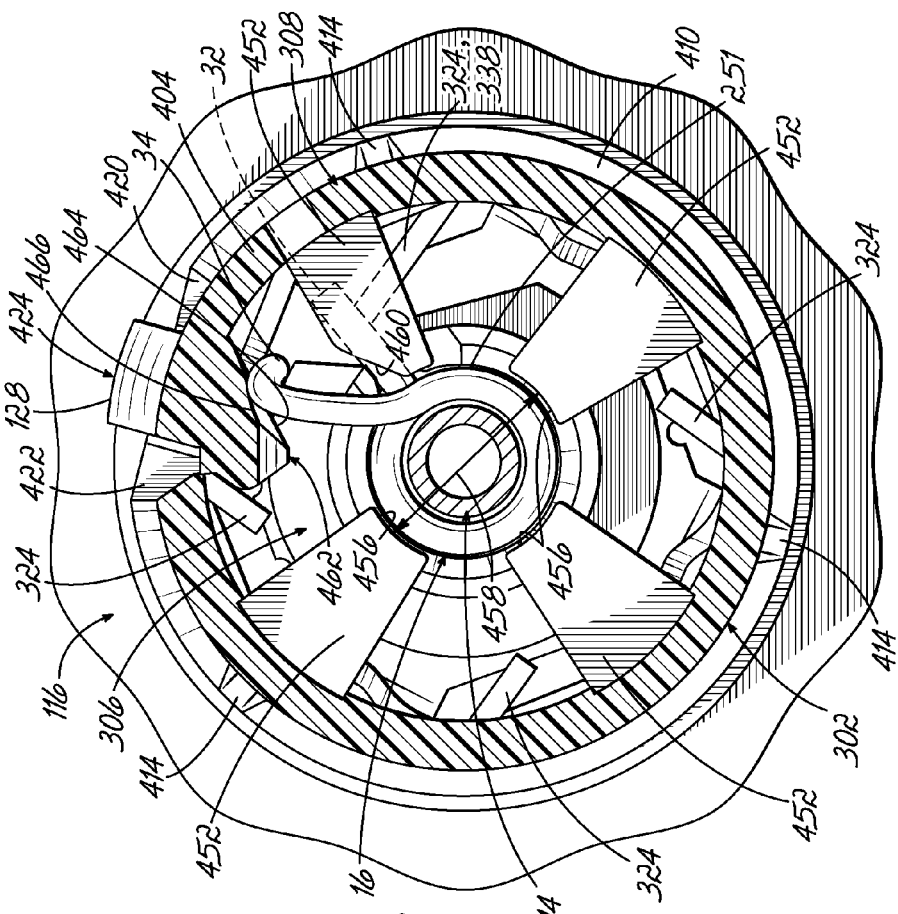
FIG. 19A is a cross-sectional view as indicated in FIG. 19.
Figure 19:
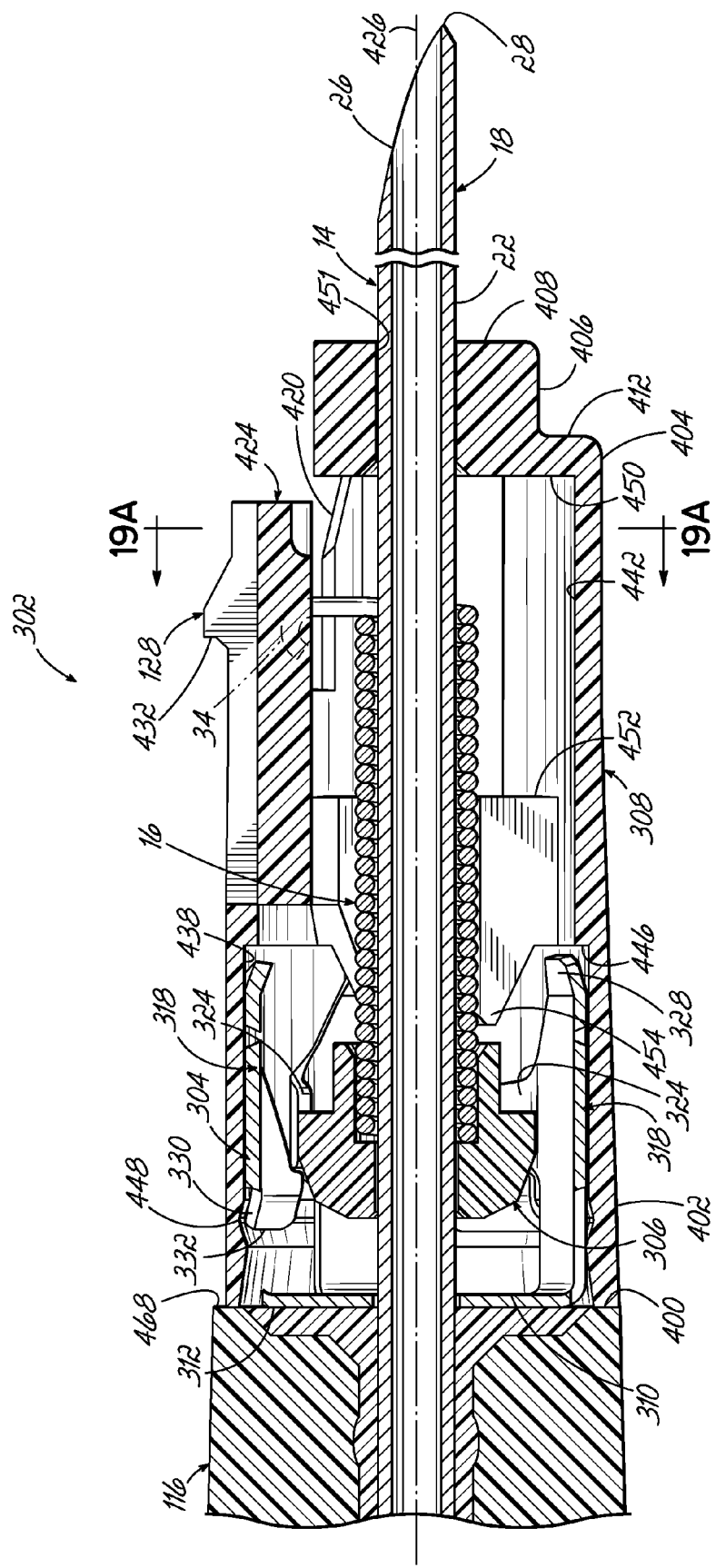
FIG. 19 is an elevational side view cross section of the needle tip spring protector of FIG. 14 in the armed state, with a cannula installed.
Figure 20:
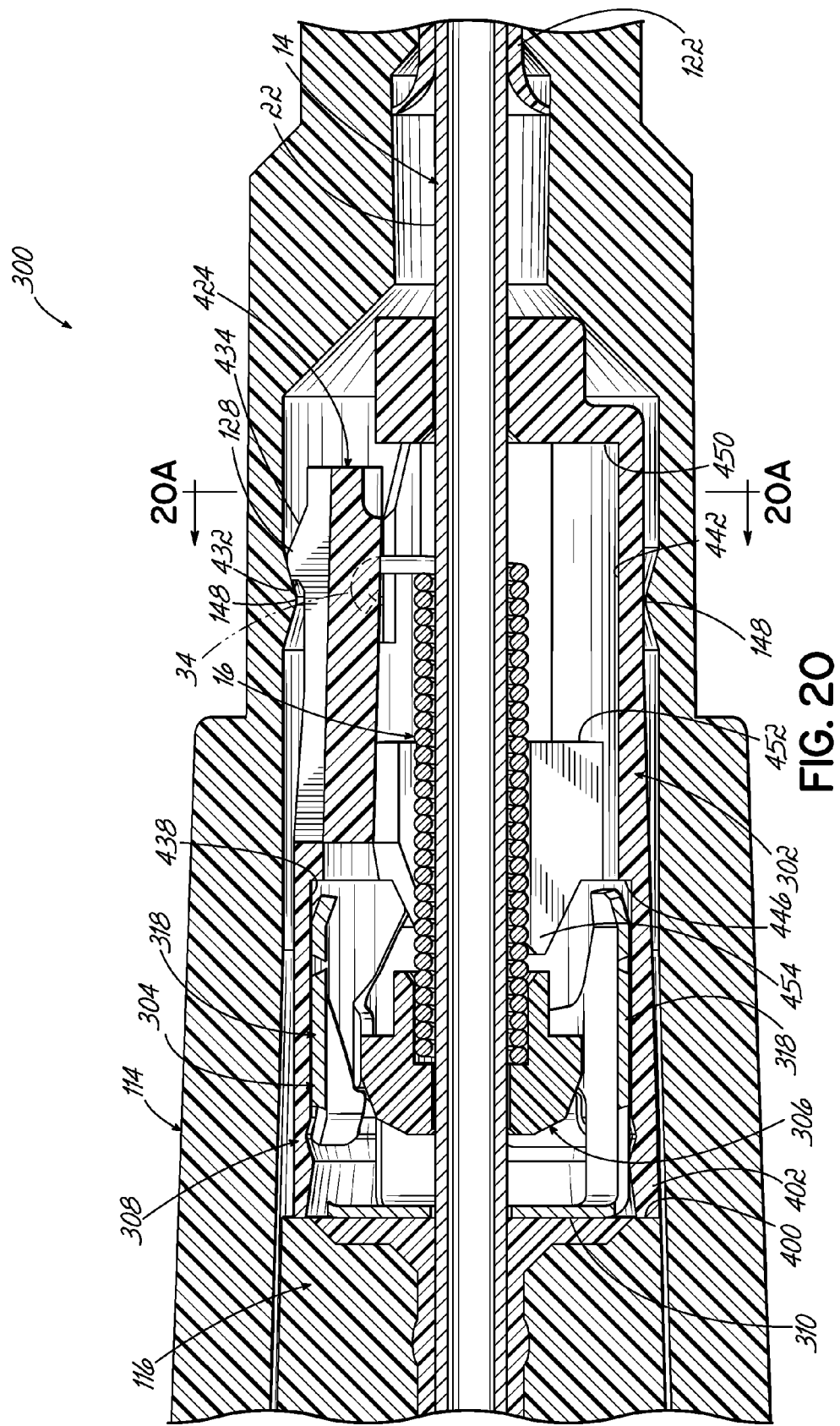
FIG. 20 is an elevational side view of part of the catheter assembly of FIG. 14.
Figure 20A:
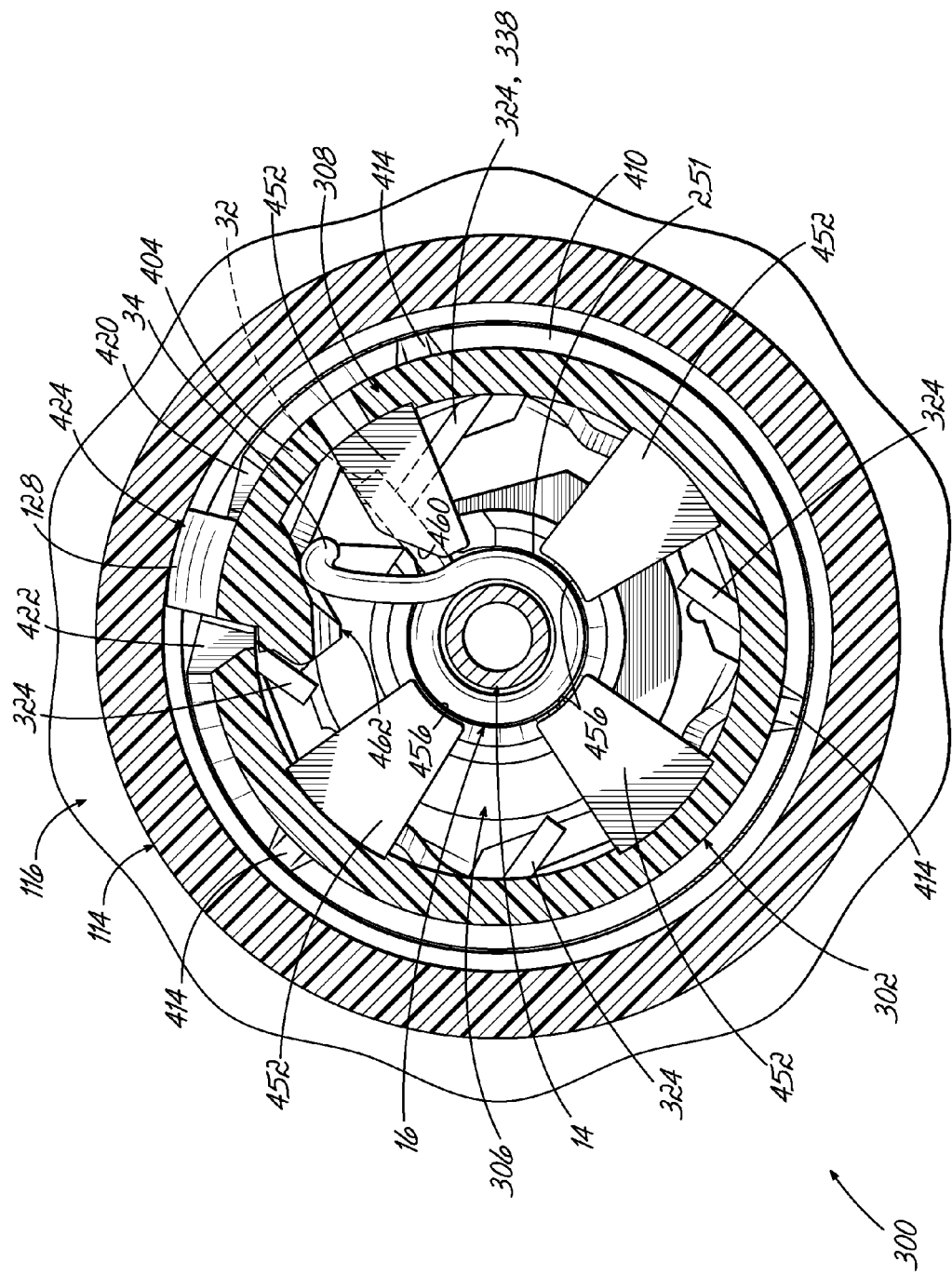
FIG. 20A is a partial cross-sectional view of as indicated in FIG. 20.

To arm the needle tip spring protector 302 (FIG. 19), the tip 18 of the needle 14 is first passed through the needle tip spring protector 302. The distal face 468 of the needle hub 116 contacts the proximal face 312 of base 310 and pushes the cup 304, washer 306, and spring 16 distally into the proximal cavity 438 and the distal cavity 442 of the housing 308 until the locking edges 332 of the arms 318 engage the annular groove 448. This movement causes the distal end 34 of spring 16 to move from the pre-arm portion 464 of the bearing surface 462 (FIGS. 18 and 18A) to the arming portion 466 (FIGS. 19 and 19A). Additionally, this movement also causes a distal end 34 of the spring 16 to move distally of the ribs 452. Although the distal end 34 of spring 16 is no longer constrained by the ribs 452, the shaft 22 of needle 16 prevents deflection of the distal end 34 away from the arming portion 466 of bearing surface 462. At this state, known as the armed state, the spring 16 is capable of unwinding and gripping to needle 14 in the manner described in the previous embodiments when actuated. While armed, the spring 16 applies an outward force to the resilient arm 424 the purpose of which will be described in more detail below. Although the arming method described above involves pushing the cup 304 into the housing 308 by using the needle hub 116, other suitable methods that move the cup 304 into the housing 308, or the housing 308 over the cup 304, while first placing the shaft 22 of needle 14 through the spring 16, would also serve to arm the needle tip spring protector 302.

To build the catheter assembly 300 (FIG. 20), the needle hub 116 and the needle tip spring protector 302, which is coaxially disposed over needle 14, are inserted into the catheter hub 114, with the lead 434 of resilient arm 424 easing the distal passing of the detent 128 over the annular protrusion 148. The annular ring 432 interacts with the annular protrusion 148, to prevent the needle tip spring protector 302 from undesirably being removed from the catheter hub 114. The ramp gussets 414 and the proximal portion 402 of housing 308 (FIG. 16) provide additional stabilization between the housing 308 and the catheter hub 114 so that any rocking, canting or other undesirable movement of the needle tip spring protector 302 inside of the catheter hub 114 is minimized. The needle hub 116 may be held in position relative to the catheter hub 114 through a snap-fit feature or in other ways that are old in the art (not shown).

Figure 21:
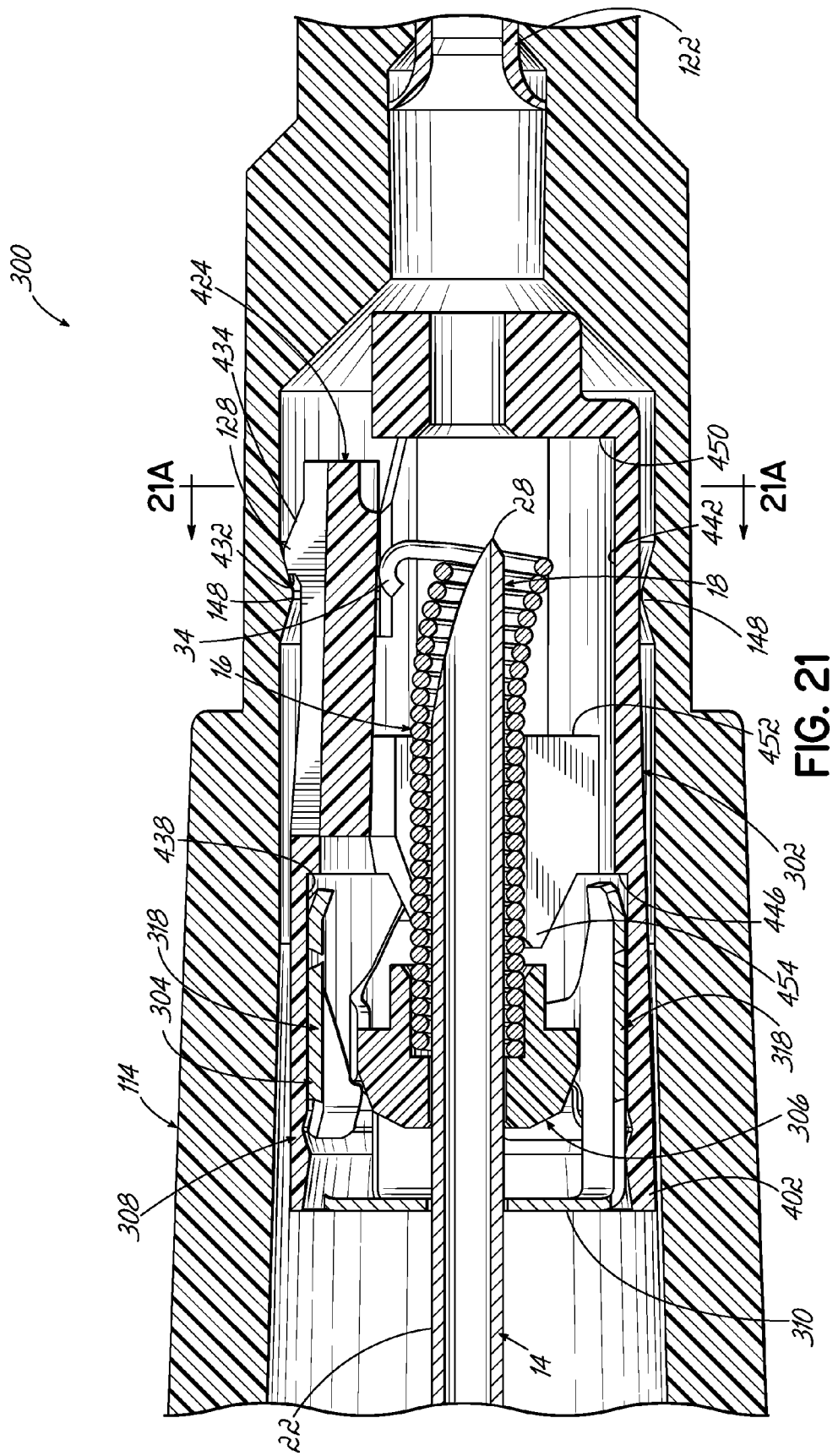
FIG. 21 is an elevational side view of part of the catheter assembly of FIG. 14, with the cannula being withdrawn and the spring protector about to fire.
Figure 21A:
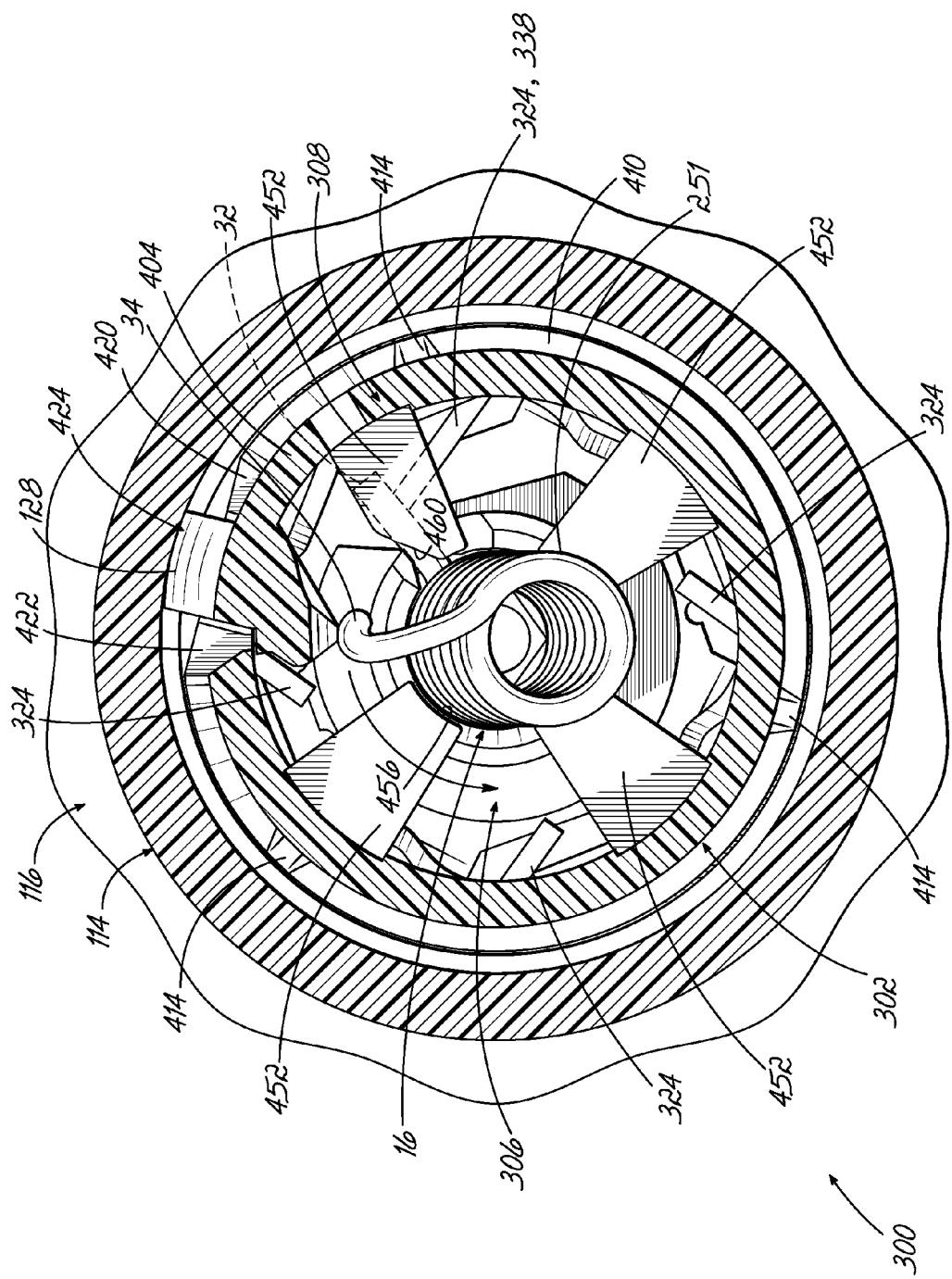
FIG. 21A is a cross-sectional view as indicated in FIG. 21.
Figure 22:
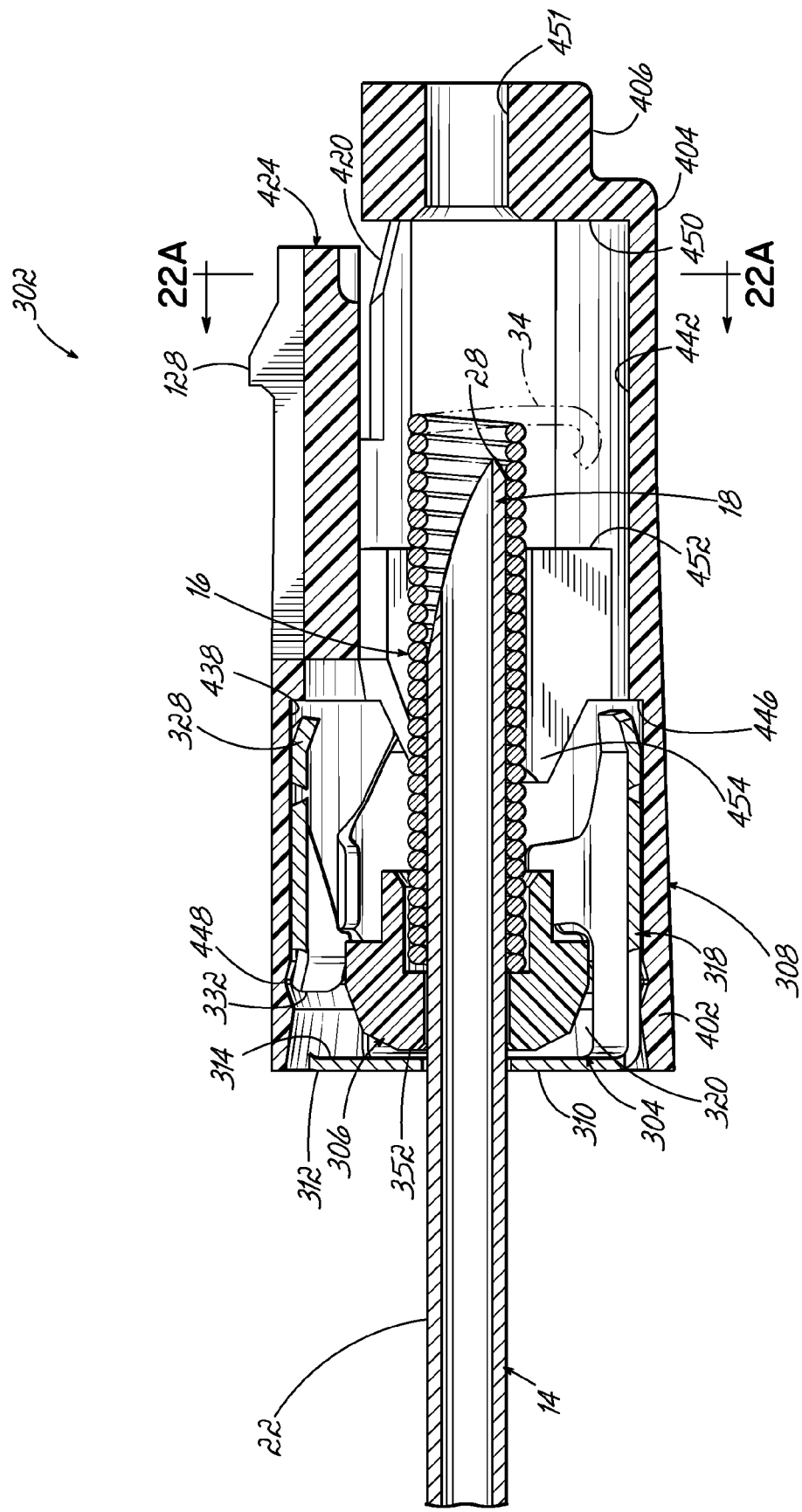
FIG. 22 is an elevational side view cross-section of the needle tip spring protector of FIG. 14 after it has fired, and been withdrawn from the catheter hub.
Figure 22A:
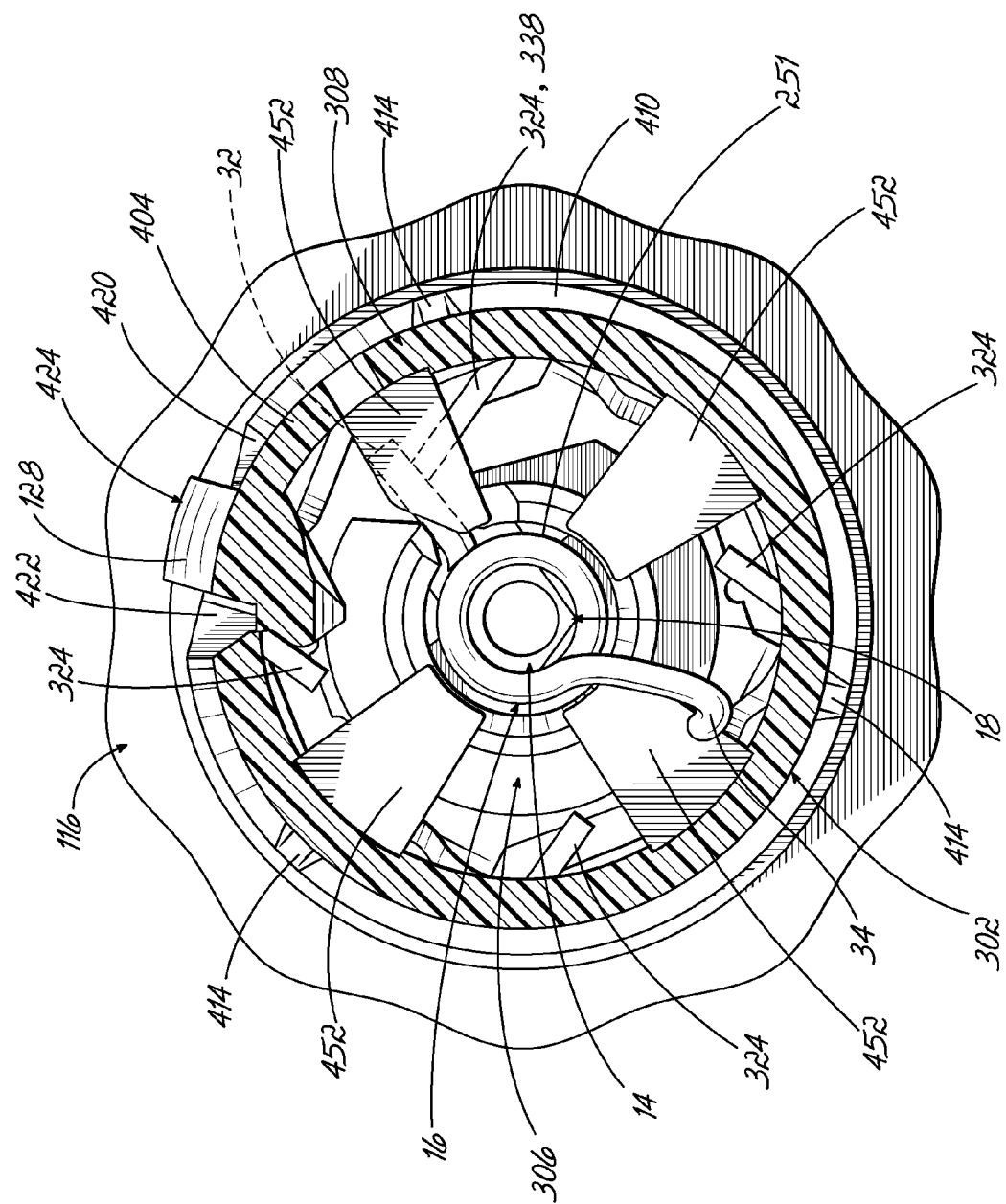
FIG. 22A is a cross-sectional view as indicated in FIG. 22.

To activate the needle tip spring protector 302 (FIGS. 21 and 21A), a healthcare worker need only use the catheter assembly 300 in the usual manner. Upon removal of the needle 14 from the patient, the region 26 of the needle 14 enters the spring 16, allowing the distal end 34 of spring 16 to deflect away from the arming portion 466 of the bearing surface 462 of the resilient arm 424. The arming portion 466 may be angled to facilitate disengagement of the distal end 34 from the arming portion 466. When the distal end 34 deflects away from the arming portion 466, the spring 16 unwinds in the direction of its rest state causing the inner diameter 36 of spring 16 to decrease or contract. As in other embodiments, the spring 16 moves towards its gripping state (FIG. 22), wherein the inside diameter 36 reaches the diameter of shaft 22 to grip shaft 22 tightly. The proximal end 32 of the spring 16, although still positioned in proximity to the notch 340, no longer has the force of the spring 16 to keep it tightly engaged therewith. Further, since the distal end 34 of spring 16 no longer bears against the resilient arm 424, the spring 16 no longer exerts a radially outward force to hold the detent 128 tightly against the inner surface 142 of catheter 114 just distal of annular protrusion 148.

To remove the needle 14 with the tip 18 thereof protected by the needle tip spring protector 302 (FIG. 22), the healthcare worker continues to move the needle hub 116 proximally by pulling in the normal manner. The needle 14 pulls the spring 16 and washer 306 proximally therewith, causing the washer 306 and spring 16 to come away from the notch 340 and move proximally into the inner chamber 320 such that the proximal face 352 of the washer 306 engages the distal face 314 of the base 310 of cup 304. Further proximal movement of the needle 14 applies a force to the cup 304, which is coupled to the housing 308 by the locking edges 332 engaging the annular groove 448. This proximally-directed force caused by pulling needle 14 is now transferred to the housing 308. The resilient arm 424 of housing 308, no longer having a force applied to it by the distal end 34 of spring 16, deflects radially inward to allow the detent 128 to move past the annular protrusion 148 and permit the housing 308 to be removed from the catheter hub 114. Accordingly, the needle tip spring protector 302 encloses the tip 18 of the needle 14 and protects the healthcare worker from inadvertent contact therewith.

A feature of this fourth embodiment is that it prevents or reduces the likelihood of accidental or intentional removal of the activated needle tip spring protector 302 by twisting of the needle 14 relative to the needle tip spring protector 302. In other words, it may be desirable to allow the needle 14 to rotate relative to the housing 308 of needle tip spring protector 302. In this embodiment, the needle tip spring protector 302 is designed to allow such relative rotation therebetween. More particularly, the washer 306 and inner chamber 320 are sized such that when the washer 306 has been pulled into the inner chamber 320 (e.g., during removal of the needle 14) the washer 306 is free to spin or rotate within the inner chamber 320. Accordingly, spring 16 remains in its gripping state regardless of the rotation of the needle 14 relative to the housing 308 of needle tip spring protector 302. In this way, the spring 16 cannot be rewound or moved back to its armed state.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, the bearing surface that restrains the distal end of the spring does not necessarily have to be flat or of any particular shape. The bearing surfaces and the distal end can be any of a variety of complimentary shapes that act to temporarily restrain the distal end while the needle is in place but which allow for the passive release of the spring when the tip moves past the distal end. Alternatively, the activation could take place prior to the tip reaching the spring, such as by using a proximal passage in the housing, and a distal passage in the housing to make the needle stable, and then making the needle and spring unstable when the needle exits the distal passage but has not yet reached the spring. This would still result in the needle tip being protected by the housing.

Additionally, a needle tip spring protector in accordance with the principles of the present invention does not necessarily have to be part of a catheter assembly. The needle tip spring protector may be part of a hypodermic needle or other, similar device. In such a configuration, the needle tip spring protector, not the catheter hub, would be moved relative to the needle such that the tip of the needle would enter the needle tip spring protector and passively activate the spring. Such a needle tip spring protector could also omit features described herein that provide for passive release from a catheter hub, as no such hub is present. Moreover, although the embodiments described use needles of standard metal finishes, and without any geometry such as notches or ridges added, needles of modified surface finishes or geometry could also be used, especially if a need to increase the gripping force of the spring on the shaft is required.

Thus, the invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A needle protection device comprising:
   a spring having a passage that extends in a longitudinal direction and has a diameter, the spring adapted to be wound and unwound to increase the diameter as the spring is wound and to decrease the diameter as the spring is unwound;
   a needle extending into the spring passage, the spring having an armed state in which the spring is sufficiently wound such that the diameter of the passage is large enough for the needle to be slidable within the passage, the spring having a gripping state in which the spring is sufficiently unwound such that the diameter of the passage is small enough to engage the needle such as to inhibit movement of the needle within the passage in the longitudinal direction; and a bearing surface positioned to cooperate with a first aspect of the spring to hold the spring in the armed state when the first aspect is bearing against the bearing surface, the spring being in substantial coaxial alignment with the needle in the armed state, wherein at least a segment of the spring moves out of substantial coaxial alignment with the needle to allow the first aspect to move away from the bearing surface, the spring movable to the gripping state when the first aspect is not bearing against the bearing surface.

2. The needle protection device of claim 1, wherein a tip of the needle is remote from the bearing surface in a first position of the needle and the tip is spaced adjacent the bearing surface in a second position of the needle.

3. The needle protection device of claim 2, wherein the needle retains the first aspect of the spring against the bearing surface when in the first position, and wherein the needle provides space between the needle and spring that allows the first aspect of the spring to move away from the bearing surface when in the second position.

4. The needle protection device of claim 1, wherein at least a portion of the spring substantially surrounds a distal end of the needle when in the gripping state.

5. The needle protection device of claim 1, further comprising a housing having the spring disposed therein and including a passage through which the needle extends in a first position of the needle, the passage of the housing being substantially axially aligned with the passage of the spring.

6. The needle protection device of claim 5, wherein the housing is slidably movable relative to the needle when the spring is in the armed state.

7. The needle protection device of claim 5, wherein the spring is fixedly secured to the housing.

8. The needle protection device of claim 5, wherein the entire spring is capable of rotating relative to the housing when the spring is in the gripping state.

9. The needle protection device of claim 5, wherein a distal end of the needle is positioned between a proximal end of the housing and the bearing surface in a second position of the needle.

10. The needle protection device of claim 5, wherein the housing includes the bearing surface.

11. A safety catheter device comprising:
a catheter tube having a distal end and a proximal end;
a catheter hub adjacent the catheter tube proximal end;
a spring having a passage that extends in a longitudinal direction and has a diameter, the spring adapted to be wound and unwound to increase the diameter as the spring is wound and to decrease the diameter as the spring is unwound;
a needle extending into the spring passage, catheter hub, and catheter tube in a first position of the needle, the spring having an armed state in which the spring is sufficiently wound such that the diameter of the passage is large enough for the needle to be slidable within the passage, the spring having a gripping state in which the spring is sufficiently unwound such that the diameter of the passage is small enough to engage the needle such as to inhibit movement of the needle within the passage in the longitudinal direction; and a bearing surface positioned to cooperate with a first aspect of the spring to hold the spring in the armed state when the first aspect is bearing against the bearing surface, the spring being in substantial coaxial alignment with the needle in the armed state, wherein at least a segment of the spring moves out of substantial coaxial alignment with the needle to allow the first aspect to move away from the bearing surface, the spring movable to the gripping state when the first aspect is not bearing against the bearing surface.

12. The safety catheter device of claim 11, wherein a tip of the needle is remote from the bearing surface in the first position of the needle and the tip is spaced adjacent the bearing surface in a second position of the needle.

13. The safety catheter device of claim 12, wherein the needle retains the first aspect of the spring against the bearing surface when in the first position, and wherein the needle provides space between the needle and spring that allows the first aspect of the spring to move away from the bearing surface when in the second position.

14. The safety catheter device of claim 11, wherein at least a portion of the spring substantially surrounds a distal end of the needle when in the gripping state.

15. The safety catheter device of claim 11, wherein the bearing surface is on the catheter hub.

16. The safety catheter device of claim 11, further comprising a housing having the spring disposed therein and including a passage through which the needle extends in the first position of the needle, the passage of the housing being substantially axially aligned with the passage of the spring.

17. The safety catheter device of claim 16, wherein the housing is slidably movable relative to the needle when the spring is in the armed state.

18. The safety catheter device of claim 16, wherein the spring is fixedly secured to the housing.

19. The safety catheter device of claim 16, wherein the entire spring is capable of rotating relative to the housing when the spring is in the gripping state.

20. The safety catheter device of claim 16, wherein a distal end of the needle is positioned between a proximal end of the housing and the bearing surface in a second position of the needle.

21. The safety catheter device of claim 16, wherein the housing includes the bearing surface.

22. The safety catheter device of claim 16, wherein the spring includes a first axial position and a second axial position relative to the housing, the first aspect of the spring contacting the bearing surface when the spring is in the second axial position, and the first aspect of the spring spaced from the bearing surface when the spring is in the first axial position.

23. The safety catheter device of claim 22, wherein the spring is in the armed state in the first and second axial positions.

24. The safety catheter device of claim 22, further comprising a ledge in the housing, wherein the first aspect of the spring contacts the ledge when the spring is in the first axial position, but moves out of contact with the ledge to contact the bearing surface when the spring is in the second axial position.

25. The safety catheter device of claim 22, further comprising a second bearing surface for confronting a second aspect of the spring.

26. The safety catheter device of claim 25, wherein the second bearing surface further comprises a notch defined by the housing.

27. The safety catheter device of claim 26, wherein the second aspect of the spring moves along a first contour of the notch when the spring moves from the first axial position to the second axial position.

28. The safety catheter device of claim 27, wherein the notch includes a narrowed portion, and wherein the second aspect of the spring moves along the first contour and through the narrowed portion as the spring moves from the first axial position to the second axial position.

29. The safety catheter device of claim 28, wherein when the second aspect of the spring is positioned distally of the narrowed portion, the second aspect cannot thereafter move proximally of the narrowed portion along the first contour.

30. The safety catheter device of claim 22, wherein the spring includes a third axial position relative to the housing, the spring being in the gripping state when in the third axial position.

31. The safety catheter device of claim 16, wherein the housing engages the catheter hub such that when the spring is in the armed state, the housing and the catheter hub are fixedly coupled together.

32. The safety catheter device of claim 31, wherein the catheter hub includes a housing-engaging element on its inner surface, and the housing includes at least one resilient member that engages the housing-engaging element when the housing and the catheter hub are fixedly coupled together.

33. The safety catheter device of claim 32, wherein the housing-engaging element is selected from the group consisting of a protrusion on the inner surface of the catheter hub, an annular protrusion around the inner surface of the catheter hub, a groove defined by the inner surface of the catheter hub, and an annular groove defined by and disposed circumferentially around the inner surface of the catheter hub.

34. The safety catheter device of claim 32, wherein the spring urges the at least one resilient member against the housing-engaging element so as to prevent the at least one resilient member from flexing away from the housing-engaging element when in the armed state, and permits the at least one resilient member to flex away from the housing-engaging element when in the gripping state.

35. The safety catheter device of claim 32, wherein the at least one resilient member is disposed proximally of a distal end of the housing.

36. The safety catheter device of claim 32, wherein the at least one resilient member contacts and confronts an outer surface of the spring when the spring is in one axial position relative to the housing.

37. The safety catheter device of claim 36, wherein when the spring has moved to the gripping state, retraction of the needle causes the spring to cooperatively move from the one axial position to another axial position relative to the housing.

38. The safety catheter device of claim 37, wherein as the spring moves from the one axial position to the another axial position, the outer surface of the spring moves out of contact with the at least one resilient member to allow the at least one resilient member to move out of engagement with the housing-engaging element.

39. A safety catheter device comprising:
a catheter tube having a distal end and a proximal end;
a catheter hub adjacent the catheter tube proximal end;
a housing adjacent the catheter hub;
a spring disposed in the housing and having a passage that extends in a longitudinal direction and has a diameter, the spring adapted to be wound and unwound to increase the diameter as the spring is wound and to decrease the diameter as the spring is unwound;
a needle extending into the housing, spring passage, catheter hub, and catheter tube in a first position of the needle, the spring having an armed state in which the spring is sufficiently wound such that the diameter of the passage is large enough for the needle to be slidable within the passage, the spring having a gripping state in which the spring is sufficiently unwound such that the diameter of the passage is small enough to engage the needle such as to inhibit movement of the needle within the passage in the longitudinal direction; and
a first bearing surface on the housing positioned to cooperate with a first aspect of the spring to hold the spring in the armed state when the first aspect is bearing against the bearing surface, the spring being in substantial coaxial alignment with the needle in the armed state, wherein at least a segment of the spring moves out of substantial coaxial alignment with the needle to allow the first aspect to move away from the bearing surface, the spring movable to the gripping state when the first aspect is not bearing against the bearing surface.

40. The safety catheter device of claim 39, further comprising a cup coupled to the housing and including a base having an aperture for receiving the needle therethrough and at least one flexible arm extending from the base.

41. The safety catheter device of claim 40, wherein the cup is movable relative to the housing between a first axial position and a second axial position, the spring capable of being placed in the armed state when the cup is in the first axial position, the first aspect of the spring contacting the bearing surface when the cup is in the second axial position.

42. The safety catheter device of claim 41, wherein the at least one flexible arm includes a first tab that engages a groove in the housing when the cup is in the first axial position.

43. The safety catheter device of claim 42, wherein the first tab is configured to cooperate with the groove to allow relative rotation between the cup and housing in a first circumferential direction and prevent relative rotation between the cup and housing in a second circumferential direction.

44. The safety catheter device of claim 42, wherein the at least one flexible arm includes a second tab that engages the groove in the housing when the cup is in the second axial position.

45. The safety catheter device of claim 44, wherein the second tab prevents relative rotation between the cup and housing.

46. The safety catheter device of claim 39, further comprising a washer coupled to the housing, the washer including a second bearing surface positioned to cooperate with a second aspect of the spring to fixedly secure the spring to the washer.

47. The safety catheter device of claim 46, wherein the washer is movable relative to the housing between a first axial position and a second axial position.

48. The safety catheter device of claim 47, wherein the spring is in the armed state when the washer is in the first axial position, and the spring is in the gripping state when the washer is in the second axial position.

49. The safety catheter device of claim 47, wherein the washer is prevented from rotating relative to the housing when in the first axial position and allowed to rotate relative to the housing when in the second axial position.

50. A safety catheter device of claim 39, further comprising a washer and a cup, wherein a second aspect of the spring is fixed to the washer and the washer is rotatably fixed to the cup and the cup is rotatably fixed to the housing when the spring is in the armed state, and the washer is capable of rotating relative to the cup when the spring is in the gripping state.

* * * * *